(12) United States Patent
Barenholz et al.

(10) Patent No.: US 9,078,812 B2
(45) Date of Patent: Jul. 14, 2015

(54) PARTICULATE DRUG CARRIERS AS DESENSITIZING AGENTS

(75) Inventors: Yechezkel Barenholz, Jerusalem (IL); Janos Szebeni, Budapest (HU); Miklos Toth, Pilisborosjeno (HU); Laszlo Rosivall, Budapest (HU)

(73) Assignees: The Bay Zoltan Foundation for Applied Research, Budapest (HU); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 507 days.

(21) Appl. No.: 12/746,656

(22) PCT Filed: Dec. 7, 2008

(86) PCT No.: PCT/IL2008/001591
§ 371 (c)(1),
(2), (4) Date: Jun. 7, 2010

(87) PCT Pub. No.: WO2009/072136
PCT Pub. Date: Jun. 11, 2009

(65) Prior Publication Data
US 2011/0097387 A1    Apr. 28, 2011

Related U.S. Application Data

(60) Provisional application No. 60/992,728, filed on Dec. 6, 2007.

(51) Int. Cl.
| *A61K 9/14* | (2006.01) |
| *A61K 9/00* | (2006.01) |
| *A61K 9/127* | (2006.01) |
| *A61K 31/337* | (2006.01) |
| *A61K 31/475* | (2006.01) |
| *A61K 31/555* | (2006.01) |
| *A61K 31/704* | (2006.01) |

(52) U.S. Cl.
CPC ............ *A61K 9/0019* (2013.01); *A61K 9/1271* (2013.01); *A61K 31/337* (2013.01); *A61K 31/475* (2013.01); *A61K 31/555* (2013.01); *A61K 31/704* (2013.01)

(58) Field of Classification Search
None
See application file for complete search history.

(56) References Cited

U.S. PATENT DOCUMENTS

| 3,993,754 A | 11/1976 | Rahman |
| 4,145,410 A | 3/1979 | Sears |
| 4,224,179 A | 9/1980 | Schneider |
| 4,235,871 A | 11/1980 | Papahadjopoulos |
| 4,522,803 A | 6/1985 | Lenk |
| 4,588,578 A | 5/1986 | Fountain |
| 4,797,285 A | 1/1989 | Barenholz |
| 5,192,549 A | 3/1993 | Barenolz |
| 5,283,185 A | 2/1994 | Epand |
| 5,316,771 A | 5/1994 | Barenholz |
| 5,616,341 A | 4/1997 | Mayer |
| 5,736,155 A | 4/1998 | Bally |
| 5,785,987 A | 7/1998 | Hope |
| 5,837,282 A | 11/1998 | Fenske |
| 5,939,096 A | 8/1999 | Clerc |
| 6,162,462 A | 12/2000 | Bolotin |
| 6,726,924 B2 | 4/2004 | Keller |
| 7,419,683 B2 | 9/2008 | Szebeni |
| 2002/0136759 A1 | 9/2002 | Szebeni |

FOREIGN PATENT DOCUMENTS

| WO | 93/03709 | 3/1993 |
| WO | 2006/042270 | 4/2006 |
| WO | 2007/049279 | 5/2007 |

OTHER PUBLICATIONS

Szebeni et al. (Journal of Liposome Research, 12 (1&2), 165-172 (2002).*
Janos Szebeni ( Toxicology 216 (2005) 106-121).*
Mayer et al. (Journal of Pharmaceutical sciences vol. 88, No. 1, 96-102, Jan. 1999).*
Adkinson, N. Franklin Jr. (2008) Desensitization for drug hypersensitivity. J Allergy Clin Immunol 122(3):581-582.
Allen, Christine et al., (1999) Nano-engineering block copolymer aggregates for drug delivery. Colloids and Surfaces B: Biointerfaces 16(1-4):3-27.
Avnir, Yuval et al., (2008) Amphipathic weak acid glucocorticoid prodrugs remote-loaded into sterically stabilized nanoliposomes evaluated in arthritic rats and in a Beagle dog: a novel approach to treating autoimmune arthritis. Arthritis Rheum 58(1):119-129.
Bangham, A. D. et al., (1965) Diffusion of univalent ions across the lamellae of swollen phospholipids. J Mol Biol 13 (1):238-252.
Brouwers, Adrienne et al., (2000) Tc-99m-PEG-Liposomes for the evaluation of colitis in Crohn's disease. J Drug Target 8(4):225-233.
Cabriales, Suzanne et al., (1998) Extravasation of liposomal daunorubicin in patients with AIDS-associated Kaposi's sarcoma: a report of four cases. Oncol Nurs Forum 25(1):67-70.
Castells, Mariana C. (2006) Desensitization for drug allergy. Curr Opin Allergy Clin Immunol 6(6):476-481.
Castells, Mariana C. (2008) Hypersensitivity reactions to chemotherapy: Outcomes and safety of rapid desensitization in 413 cases. J Allergy Clin Immunol 122(3):574-580.
Chanan-Khan, A. et al., (2003) Complement activation following first exposure to pegylated liposomal doxorubicin (Doxil®): possible role in hypersensitivity reactions. Ann Oncol 14(9):1430-1437.

(Continued)

*Primary Examiner* — Snigdha Maewall
(74) *Attorney, Agent, or Firm* — Rodney J. Fuller; Booth Udall Fuller, PLC

(57) ABSTRACT

The present invention provides methods for desensitization for prevention or diminishing hypersensitivity reactions including C activation-related pseudoallergy (CARPA) and other reactions to particulate medicines. The desensitization is performed via pretreatment using a drug-free vehicle or carrier to eliminate or diminish the clinical symptoms of hypersensitivity.

10 Claims, 13 Drawing Sheets

(56) References Cited

OTHER PUBLICATIONS

Cheifetz, Adam and Mayer, Lloyd (2005) Monoclonal antibodies, immunogenicity, and associated infusion reactions. Mt Sinai J Med 72(4):250-256.
Clerc, Stephane and Barenholz, Yechezkel (1995) Loading of amphipathic weak acids into liposomes in response to transmembrane calcium acetate gradients. Biochim Biophys Acta 1240(2):257-265.
Deamer, D. and Bangham, A. D. (1976) Large volume liposomes by an ether vaporization method. Biochim Biophys Acta 443(3):629-634.
Descotes, Jacques and Choquet-Kastylevsky, Genevieve (2001): Gell and Coombs's classification: Toxicology 158(1-2):43-49.
Eierman, David F. et al., (1995) Endogenously opsonized particles divert prostanoid action from lethal to protective in models of experimental endotoxemia. Proc Natl Acad Sci USA 92(7):2815-2819.
Feldweg, Anna M. et al., (2005) Rapid desensitization for hypersensitivity reactions to paclitaxel and docetaxel: a new standard protocol used in 77 successful treatments. Gynecol Oncol 96(3):824-829.
Garbuzenko, Olga et al., (2005) Electrostatics of pegylated micelles and liposomes containing charged and neutral lipopolymers. Langmuir 21(6):2560-2568.
Guaglianone, Perry et al., (1994) Phase I and pharmacologic study of liposomal daunorubicin (DaunoXome). Invest New Drugs 12(2):103-110.
Haran, Gilad et al., (1993) Transmembrane ammonium sulfate gradients in liposomes produce efficient and stable entrapment of amphipathic weak bases. Biochim Biophys Acta 1151(2)201-215.
Kirby, Christopher and Gregoriadis, Gregory (1984) Dehydration-Rehydration Vesicles: A Simple Method for High Yield Drug Entrapment in Liposomes. Nat Biotechnol 2(11):979-984.
Kirschfink, Michael (1997) Controlling the complement system in inflammation. Immunopharmacology 38 (1-2):51-62.
Lavasanifar, Afsaneh et al., (2000) Micelles of poly(ethylene oxide)-block-poly(N-alkyl stearate L-aspartamide): synthetic analogues of lipoproteins for drug delivery. J Biomed Mater Res 52(4):831-835.
Lenz, Heinz-Josef (2007) Management and preparedness for infusion and hypersensitivity reactions. Oncologist 12 (5):601-609.
Lewis, Russell E. et al., (2007) Pretreatment with empty liposomes attenuates the immunopathology of invasive pulmonary aspergillosis in corticosteroid-immunosuppressed mice. Antimicrob Agents Chemother 51(3):1078-1081.
Mayer, Lawrence D. et al., (1999) Intravenous pretreatment with empty pH gradient liposomes alters the pharmacokinetics and toxicity of doxorubicin through in vivo active drug encapsulation. J Pharm Sci 88(1):96-102.
Moghimi, S. Moein et al., (2006) Activation of the human complement system by cholesterol-rich and PEGylated liposomes-modulation of cholesterol-rich liposome-mediated complement activation by elevated serum LDL and HDL levels. J Liposome Res 16(3):167-174.
Moghimi, S. Moein et al., (2006) Methylation of the phosphate oxygen moiety of phospholipid-methoxy(polyethylene glycol) conjugate prevents PEGylated liposome-mediated complement activation and anaphylatoxin production. FASEB J 20(14):2591-2593.
Perkins, Walter R. et al., (2000) Novel therapeutic nano-particles (lipocores): trapping poorly water soluble compounds. Int J Pharm 200(1):27-39.
Shew, R. R L. and Deamer, D. W. (1985) A novel method for encapsulation of macromolecules in liposomes. Biochim Biophys Acta 816(1):1-8.
Soloviev, A. I. et al., (2002) Saline containing phosphatidylcholine liposomes possess the ability to restore endothelial function damaged resulting from gamma-irradiation. J Physiol Pharmacol 54(4 pt1):701-712.
Soppimath, Kumaresh S. et al., (2001) Biodegradable polymeric nanoparticles as drug delivery devices: J Control Release 70(1-2):1-20.

Szebeni, Janos et al., (1999) Hemodynamic changes induced by liposomes and liposome-encapsulated hemoglobin in pigs: a model for pseudo-allergic cardiopulmonary reactions to liposomes. Role of complement and inhibition by soluble CR1 and anti-C5a antibody. Circulation 99(17):2302-2309.
Szebeni, Janos et al., (2000) Liposome-induced pulmonary hypertension: Properties and mechanism of a complement-mediated pseudoallergic reaction. Am J Physiol 279(3):H1319-H1328.
Szebeni, Janos et al., (2000) The Role of Complement Activation in Hypersensitivity to Pegylated Liposomal Doxorubicin (Doxil®). J Liposome Res 10(4):467-481.
Szebeni, Janos et al., (2001) Formation of complement-activating particles in aqueous solutions of Taxol: Possible role in hypersensitivity reactions. Int Immunopharmacol 1(4):721-735.
Szebeni, J. (2001) Complement activation-related pseudoallergy caused by liposomes, micellar carriers of intravenous drugs and radiocontrast agents. Crit Rev Ther Drug Carrier Syst 18(6):567-606.
Szebeni, J. et al., (2002) Role of complement activation in hypersensitivity reactions to doxil and hynic PEG liposomes: experimental and clinical studies. J Liposome Res 12(1-2):165-172.
Szebeni, J. et al., (2003) The Interaction of Liposomes with the Complement System: In Vitro and In Vivo Assays. Methods Enzymol 373:136-154.
Szebeni, J. (2004): Complement activation-related pseudoallergy: Mechanism of anaphylactoid reactions to drug carriers and radiocontrast agents, pp. 399-440. In: J. Szebeni (Ed.): the Complement System: Novel Roles in Health and Disease, Kluwer, Boston.
Szebeni, Janos (2005) Complement activation-related pseudoallergy: a new class of drug-induced acute immune toxicity. Toxicology 216(2-3):106-121.
Szebeni, J. et al., (2006) Complement activation-related cardiac anaphylaxis in pigs: role of C5a anaphylatoxin and adenosine in liposome-induced abnormalities in ECG and heart Function. Am J Physiol Heart Circ Physiol 290(3): H1050-H1058.
Szebeni, Janos et al., (2007) Animal models of complement-mediated hypersensitivity reactions to liposomes and other lipid-based nanoparticles. J Liposome Res 17(2):107-117.
Szebeni, Janos and Alving, Carl R. (1999) Complement-mediated acute effects of liposome-encapsulated hemoglobin. Artif Cells Blood Substit Immobil Biotechnol 27(1):23-41.
Szoka, Francis Jr. and Papahadjopoulos, Demetrio (1978) Procedure for preparation of liposomes with large.
Szoka, F. Jr. and Papahadjopoulos, D. (1980) Comparative Properties and Methods of Preparation of Lipid Vesicles (Liposomes). Annu Rev Biophys Bioeng 9:467-508.
Tirosh, Oren et al., (1998) Hydration of polyethylene glycol-grafted liposomes. Biophys J 74(3):1371-1379.
Uster, Paul S. et al., (1996) Insertion of poly(ethylene glycol) derivatized phospholipid into pre-formed liposomes results in prolonged in vivo circulation time. FEBS Letters 386(2-3):243-246.
Veronese, F. M. and Morpurgo, M. (1999) Bioconjugation in pharmaceutical chemistry. Farmaco 54(8):497-516.
Zuidam Nicolaas J. and Barenholz, Yechezkel (1997) Electrostatic parameters of cationic liposomes commonly used for gene delivery as determined by 4-heptadecyl-7-hydroxycoumarin. Biochim Biophys Acta 1329(2):211-222.
ISR PCT/IL2008/001591 mailed Apr. 9, 2009.
Barenholz (2001) Liposome application: problems and prospects. Curr Opin Colloid Interface Sci 6: 66-77.
Fossa et al., (1998) A phase II study of DaunoXome in advanced urothelial transitional cell carcinoma. Eur J Cancer 34 (7): 1131-2.
Gabizon et al., (1994a) Prolonged circulation time and enhanced accumulation in malignant exudates of doxorubicin encapsulated in polyethylene-glycol coated liposomes. Cancer Res 54: 987-992.
Gabizon et al., (1994b) Clinical studies of liposome-encapsulated doxorubicin. Acta Oncol 33(7): 779-86.
Gabizon et al., (2003) Pharmacokinetics of pegylated liposomal Doxorubicin: Review of animal and human studies. Clin Pharmacokinet 42(5): 419-36.
Gill et al., (1995) Phase I/II clinical and pharmacokinetic evaluation of liposomal daunorubicin. J Clin Oncol 13(4): 996-1003.

(56) References Cited

OTHER PUBLICATIONS

Gill et al., (1996) Randomized phase III trial of liposomal daunorubicin versus doxorubicin, bleomycin, and vincristine in AIDS-related Kaposi's sarcoma. J Clin Oncol 14(8): 2353-64.
Laing et al., (1994) Anaphylactic reactions to liposomal amphotericin. The Lancet 344(8923): 682.
Levine et al., (1991) Cardiopulmonary toxicity after liposomal amphotericin B infusion. Ann Intern Med 114(8): 664-6.
Money-Kyrle et al., (1993) Liposomal daunorubicin in advanced Kaposi's sarcoma: a phase II study. Clin Oncol (R Coll Radiol) 5(6): 367-71.
Richardson et al., (1997) Early evaluation of liposomal daunorubicin (DaunoXome, Nexstar) in the treatment of relapsed and refractory lymphoma. Invest New Drugs 15(3): 247-53.
Ringdén et al., (1994) Allergic reactions and other rare side effects of liposomal amphotericin. Lancet 344(8930): 1156-7.
Schneider et al., (1998) Anaphylactic reaction to liposomal amphotericin (AmBisome). Br J Haematol 102(4): 1108-9.
Szebeni (2004) Complement Activation-Related Pseudoallergy: Mechanism of Anaphylactoid Reactions to Radiocontrast Media and Drug Carrier Liposomes and Micelles. In: The Complement System: Novel Roles in Health and Disease, J. Szebeni (Ed.), Kluwer, Boston, pp. 361-396.
Szebeni et al., (1994) Complement activation in rats by liposomes and liposome-encapsulated hemoglobin: evidence for anti-lipid antibodies and alternative pathway activation Biochem Biophys Res Commun 205(1): 255-63.
Szebeni et al., (1996) Complement activation in human serum by liposome-encapsulated hemoglobin: the role of natural anti-phospholipid antibodies. Biochim Biophys Acta 1285(2): 127-30.
Szebeni et al., (1997a) Complement activation and thromboxane A2 secretion in rats following administration of liposome-encapsulated hemoglobin: Inhibition by soluble complement receptor type 1. Art Cells Blood Subs and Immob Biotechnol 25: 379-392.
Szebeni et al., (1997b) Complement activation in vitro by the red blood cell substitute, liposome-encapsulated hemoglobin: Mechanism of activation and inhibition by soluble complement receptor type 1. Transfusion. 37(2): 150-9.
Szebeni et al., (1998) Complement activation by Cremophor EL as a possible contributor to hypersensitivity to paclitaxel: an in vitro study. J Natl Cancer Inst 90(4): 300-6.
Tulpule et al., (1998) Phase II trial of liposomal daunorubicin in the treatment of AIDS-related pulmonary Kaposi's sarcoma. J Clin Oncol 16(10): 3369-74.
Uziely et al., (1995) Liposomal doxorubicin: antitumor activity and unique toxicities during two complementary phase I studies. J Clin Oncol 13(7): 1777-85.

\* cited by examiner

Paradoxical bradycardia
AV block, asystolia

Ventricular Fibrillation,
ST-depression

PARTICULATE DRUG CARRIERS AS DESENSITIZING AGENTS

RELATED APPLICATION DATA

This application is the U.S. National Stage of PCT/IL2008/001591 filed Dec. 7, 2008, which claims the benefit of U.S. Provisional Application No. 60/992,728, filed Dec. 6, 2007, the contents of each of which are herein incorporated by reference for all purposes.

FIELD OF THE INVENTION

The present invention relates to desensitization with placebo drug carriers to prevent hypersensitivity reactions to liposomal drugs and other particulate and nano-medicines.

BACKGROUND OF THE INVENTION

Hypersensitivity to Particle-Containing Medicines

It is well known in clinical practice that intravenous infusion of some drugs or diagnostic agents containing particles with diameter in the nano- to micrometer ($10^{-9}$-$10^{-6}$ m) range, commonly called particulate medicines (PCM), can cause an acute transient illness referred to as hypersensitivity, or infusion reaction. The symptoms of these "PCM reactions" are similar to those seen in common pollen or food allergies. Some of these symptoms may, however, be unique and cannot be explained by the classic IgE paradigm of allergy, nor can they be diagnosed or predicted by conventional in vivo or in vitro allergy tests (e.g., skin tests or plasma IgE measurements; Szebeni, 2001). The clinical picture of PCM-caused "pseudoallergy", analogous to IgE-mediated allergy, shows great individual variation in severity and is accompanied by a spectrum of symptoms. In the most severe forms of the syndrome, the symptoms closely resemble anaphylaxis, a special form of life-threatening immunogenic shock. Severe PCM reactions are thus referred to as anaphylactic, or anaphylactoid. Yet another term is idiosyncrasy, reflecting the oddness of these reactions.

There is increasing evidence that a major contributing cause of PCM reactions, is activation of the complement system (C) which is part of the nonspecific, humoral arm of the immune system. Activation of this cascade system leads to the formation of anaphylatoxins (C3a, C5a), potent triggers of a range of inflammatory mediators including histamine, serotonin, bradykinin, chemotactic factors, proteases, prostaglandins, thromboxanes, leukotrienes and a range of cytokines, which act on smooth muscle cells, endothelial cells and other blood cells, causing the symptoms of hypersensitivity reactions (Szebeni, 2001; Szebeni, 2004; Szebeni et al., 2006). A recently proposed re-classification of hypersensitivity is schematically presented in FIG. 1. Allergic or hypersensitivity reactions have traditionally been classified into four categories called Type I-IV (Coombs and Gell, 1968). An increasing need to update this system to cover, for example, pseudoallergy, laid out a functional categorization that differentiates acute (Type I) hypersensitivity reactions according to the underlying mechanism of mast cell and basophil release reactions (Descotes and Choquet-Kastylevsky, 2001). The scheme differentiates two major subclasses, namely the direct cell activation and the receptor-mediated activation. The latter category further encompasses three subcategories: a) IgE-triggered and FCγIII receptor mediated, b) anaphylatoxin-triggered and C3a/C5a receptor-mediated complement activation-related pseudoallergy ("CARPA"), and c) mixed type reactions, triggered by both IgE and anaphylatoxins.

While the molecular mechanism of PCM-triggered CARPA is complex, the underlying cause is the same: to eliminate from the blood particles whose shape and size resemble pathogenic microbes, (e.g., viruses, small fungi including yeasts, protozoans, and bacteria). The complement (C) system has evolved through phylogeny as an immediate acting, first-line immune defense against blood-borne microorganisms, with three main pathways of activation: classical, lectin and alternative. In the first pathway, the microbial target and host recognition molecule that ensures selective triggering of C attack, are foreign antigens and self-antibodies, respectively. In the lectin pathway, it is the microbial mannose-containing glycoproteins and host mannose binding lectin that serve these functions. The third pathway provides much less specificity to the engagement of the C system. In this alternative pathway, the underlying mechanism is constant formation and binding of C3b to free amino- and carboxyl groups on membrane surfaces, indiscriminately on all cells and particles, except those host cells that express surface inhibitors of C activation (CR1, DAF, MCP and CD59; Kirschfink, 1997).

Liposomes, micelles and other particulate reactogenic drug carriers do not carry such C inhibitors on their surface. They thus activate C via the alternative pathway, with or without additional involvement of the first two pathways.

Liposome Reactions and the Role of Complement

Phospholipid vesicles, or liposomes, are increasingly used in medicine for targeted delivery or controlled release of various drugs and diagnostic agents. They can substantially alter the absorption, distribution, metabolism and excretion of the encapsulated drugs or agents, improving their efficacy and/or reducing their toxicity. There are many liposomal formulations or lipid-based products in the market, including but not limited to, Doxorubicin in liposomal carriers for treating cancer, Daunorubicin in liposomal carriers for treating advanced HIV-associated Kaposi's sarcoma, and Amphotericin B in liposomes and other lipid assemblies for treating systemic fungal infections. Additional liposome based drugs were approved by FDA and many more liposome or lipid-based drugs are in clinical development, including but not limited to, Verteporfin, all-trans-retinoic acid (ATRA), Oxaliplatin, Vincristine, Topotecan, Vinorelbine, Paclitaxel, Mitoxantrone, c-raf antisense, CPT-11 and others.

A significant disadvantage of using liposome or lipid-based drugs is the induction of acute hypersensitivity reactions in a high percentage (up to 45%) of patients, with hemodynamic, respiratory and cutaneous manifestations. Acute hypersensitivity reactions have been reported, among others, for liposomal doxorubicin, (e.g. DOXIL™, CAELYX™), liposomal amphotericin B (e.g. AMBISOME™, ABELCET™) and liposomal daunorubicin (e.g. DAUNOXOME™). Clinical evidence for the causal relationship between C activation and hypersensitivity reactions (CARPA) to liposomes was provided by Brouwers et al. (2000), who reported 16-19% decrease of plasma C3, C4 and factor B in the blood of a patient developing hypersensitivity to $^{Tc-99m}$HYNIC-PE-containing pegylated liposomes, applied for the scintigraphic detection of infection and inflammation. In another study, Chanan-Khan et al. (2001) found significant correlation between plasma terminal complex (SC5b-9) levels and manifestations of hypersensitivity reactions in cancer patients treated with DOXIL™ for the first time.

Diagnostic and Predictive Tests of Liposomal CARPA

There are numerous in vitro and in vivo tests for the demonstration, quantification and prediction of liposomal CARPA, including 1) measurement of C split products (C3a, C5a, SC5b-9) in human serum incubated with the reactogenic test drug, 2) measurement of leukocyte and/or mast cell activation in whole blood in the presence of test drug, and 3) detection and/or measurement of the cardiopulmonary and hemodynamic changes (hyper and/or hypotension, bradycardia, tachycardia, pulmonary hypertension, arrhythmia, symptoms of dyspnea, e.g., paling of the tongue, lip, skin changes, such as rash) in animals following i.v. injection of the reactogenic drug (Szebeni et al., 2006; Szebeni et al., 2003). There are also indications that C activation lead to hyper coagulation.

Prevention and Treatment of CARPA

Several methods for the prevention and treatment of CARPA associated with the administration of particulate medicines were suggested. Among those a method disclosed by U.S. Pat. No. 7,419,683 which teaches the administration of a complement activation inhibitor with the amphiphillic carrier encapsulated drug and a study showing that extensive methylation of the phospholipid-methoxy(polyethylene glycol) of PEGylated liposomes is effective in preventing CARPA (Moghimi S. M. et. al., 2007).

However, to date, the treatment modalities available for preventing or reducing pseudoallergic reactions in general, and CARPA in particular, include premedication with antihistamines and corticosteroids, and/or a reduction of the administration rate of a putative pseudoallergenic drug. In severe cases discontinuation of drug administration is required with or without supportive therapy, which include the use of fluids and bronchodilators (epinephrine and others) (Heinz-Josef Lenz, 2007). While partially effective, neither of these measures provide specific and full protection against these reactions.

Hence, there is an unmet need for preventing hypersensitivity reactions to liposomal drugs and other particulate (nano) medicines, particularly intravenously administered.

SUMMARY OF THE INVENTION

The present invention provides methods for preventing or diminishing hypersensitivity reactions associated with the administration of a reactogenic pharmaceutical composition, specifically pharmaceutical compositions comprising particulate vehicles or carriers. The methods of the present invention confer protection via desensitization. According to some embodiments the methods prevent or diminish the complement activation-related pseudoallergy (CARPA) and other hypersensitivity or allergic reactions. The procedures of the invention comprise pretreatment with placebo drug carrier, prior to the administration of the reactogenic pharmaceutical composition. According to some embodiments, the placebo is a drug-free carrier. According to alternative embodiments the placebo is a vehicle or carrier containing the active ingredient of the reactogenic pharmaceutical composition in subtherapeutic doses.

According to the present invention it is now disclosed for the first time that experimental animals treated with drug free liposomes equivalent to the liposomes encapsulating the drug doxorubicin, did not develop the symptoms of immediate hypersensitivty reactions seen routinely shortly after administration of even minute amounts of DOXIL™. The drug free liposomes corresponding to DOXIL™ are referred to herein after as Doxebo. The present invention is based in part on the surprising discovery that pigs treated with Doxebo showed no increase of the pulmonary arterial pressure (PAP) after subsequent intravenous administration of DOXIL™. Desensitization with drug free placebo liposomes was effective and specific in preventing the hypersensitivity reaction caused by subsequent administration of therapeutically effective doses of DOXIL™.

According to one aspect, the present invention provides a method for treating an individual who is at risk of having hypersensitivity reactions associated with the administration of a reactogenic pharmaceutical composition comprising pretreatment by means of administering the vehicle or carrier, wherein said vehicle or carrier is a drug-free carrier, prior to the administration of the reactogenic pharmaceutical composition. According to another aspect of the present invention the method for treating an individual at risk of having hypersensitivity reactions associated with the administration of a reactogenic pharmaceutical composition comprises pretreatment by means of administering the vehicle or carrier, wherein said vehicle or carrier contains an active ingredient in subtherapeutic dose, prior to the administration of the reactogenic pharmaceutical composition.

The terms "treating" and "treatment" as used herein are aimed at prevention i.e., prophylaxis. Thus, the methods of the present invention are useful in preventing or reducing the severity of symptoms of hypersensitivity reactions in an individual at a risk of having hypersensitivity reactions. According to one embodiment the individual is a mammal. According to another embodiment, the mammal is human.

According to one embodiment the hypersensitivity reaction is an immediate hypersensitivity or type I allergy and comprises the complement system activation-related pseudoallergy (CARPA). According to another embodiment said hypersensitivity is manifested in a broad array of abnormal physiological conditions selected from anaphylaxis, anaphylactic reactions, anaphylactoid reactions, pseudoallergy, infusion reactions and idiosyncratic reactions wherein the associated symptoms may be acute or subacute and may vary from mild to severe, life threatening or even deadly.

According to some embodiments the reactogenic particulate pharmaceutical composition as used herein, comprises a vehicle or a carrier and an active ingredient. According to other embodiments the active ingredient is selected from a drug and a diagnostic agent. According to some further embodiments the drug is selected from anthracylines such as doxorubicin and daunorubicin, amphotericin B, verteporfin, oxaliplatin, Vinca alkaloids such as vincristine and vinorelbine, camptothecins such as topotecan and CTP-11, paclitaxel, mitoxantrone, c-raf antisense and. According to some preferred embodiments the drug is selected from doxorubicin, daunorubicin and amphotericin B.

According to one embodiment the carriers of the present invention are selected from liposomes and micelles. According to another embodiment the carriers are selected from: nanocapsules, nanospheres, block copolymer micelles, lipid stabilized emulsions, polymer lipid hybrid systems and derivatized single chain polymers. According to further embodiment the carriers are selected from carbon or other nanotubes. According to yet another embodiment, the carrier is selected from dendrimers, fullerenes and buckyballs. According to yet another embodiments the vehicle or carrier of the present invention are selected from antibodies and proteins.

According to a further embodiment the liposomal carriers comprise stabilizing polymers. In a preferred embodiment the stabilizing polymers consists of polyethylene glycol (PEG) having a molecular weight in the 350-100,000 dalton range.

According to another embodiment the micellar carriers are selected from lipid micelles, lipoprotein micelles and polymeric micelles.

A common feature of these vehicles or carriers is that they are responsible, directly, or indirectly, partly or fully, for the immune reactogenicity (complement activation or other type of immune stimulation) of the pharmaceutical formulation. In other words, hypersensitivity reactions may to some extent be induced by the vehicle or carrier alone, by some of its components or by the pharmaceutical composition comprising an active ingredient and the vehicle or carrier. Without wishing to be bound by any theory or mechanism of action, the above pretreatment may induce a sub-clinical reaction or may cause other immune changes that reduce sensitivity to subsequently administered reactogenic pharmaceutical compositions. As a result, the reaction caused by the reactogenic pharmaceutical composition administered subsequently to the placebo pretreatment is either absent or significantly diminished. Thus, the pretreatment according to the principles of the present invention desensitizes an individual against hypersensitivity reactions caused by the reactogenic pharmaceutical composition.

According to some embodiments, the route of administering the placebo to an individual is any route where the particulate material reaches the blood stream. Suitable routes are selected from the group consisting of intramuscular, intraperitoneal, intravenous, subcutaneous, intranasal and oral. According to some currently preferred embodiments, the placebo is administered intravenously.

According to some embodiments of the present invention, the placebo is administered not more than 7 days prior to the administration of the reactogenic particulate pharmaceutical composition. According to some preferred embodiments, the placebo is administered not more than 24 hours prior to the administration of the reactogenic particulate pharmaceutical composition. According to further preferred embodiments, the placebo is administered not more than an hour prior to the administration of the reactogenic particulate pharmaceutical composition. According to the most preferred embodiment, the placebo is administered not more than 20 minutes prior to the administration of the reactogenic particulate pharmaceutical composition.

According to some additional embodiments the placebo is administered at least once prior to the administration of the reactogenic pharmaceutical composition.

According to another aspect, the present invention provides use of a drug-free vehicle or carrier for the preparation of a medicament for the prevention or reduction of hypersensitivity reactions associated with administration of a reactogenic particulate pharmaceutical composition, wherein the drug-free vehicle or carrier is substantially the same as the vehicle or carrier of the reactogenic particulate pharmaceutical composition. According to one preferred embodiment this medicament is adapted for administration prior to the administration of the reactogenic pharmaceutical composition.

According to another aspect, the present invention provides use of a drug vehicle or carrier comprising an active ingredient in subtherapeutic dose for the preparation of a medicament for the prevention or reduction of hypersensitivity reactions associated with administration of a reactogenic pharmaceutical composition, wherein the drug vehicle or carrier is substantially the same as the vehicle or carrier of the reactogenic particulate pharmaceutical composition and wherein the reactogenic particulate pharmaceutical composition comprises the active ingredient in a therapeutic dose. According to one preferred embodiment this medicament is adapted for administration prior to the administration of the reactogenic pharmaceutical composition.

According to yet another aspect, the present invention provides a drug-free vehicle or carrier for use in treating hypersensitivity reactions associated with the administration of a reactogenic particulate pharmaceutical composition, wherein the drug-free vehicle or carrier is substantially the same as the vehicle or carrier of the reactogenic particulate pharmaceutical composition. According to a preferred embodiment this drug free vehicle or carrier is adapted for administration prior to the administration of the reactogenic particulate pharmaceutical composition.

According to yet another aspect, the present invention provides a drug vehicle or carrier comprising an active ingredient in subtherapeutic dose for use in treating hypersensitivity reactions associated with the administration of a reactogenic particulate pharmaceutical composition, wherein the drug vehicle or carrier is substantially the same as the vehicle or carrier of the reactogenic particulate pharmaceutical composition and wherein the reactogenic particulate pharmaceutical composition comprises the active ingredient in a therapeutic dose. According to a preferred embodiment this drug vehicle or carrier is adapted for administration prior to the administration of the reactogenic particulate pharmaceutical composition.

According to some embodiments the placebo vehicle or carrier may need to be essentially identical to the vehicle or carrier of the reactogenic particulate pharmaceutical composition. According to other embodiments the placebo need not be identical to the vehicle or carrier of the reactogenic pharmaceutical composition in order to achieve the desired effect. According to certain embodiments, the placebo is similar to the vehicle or carrier of the reactogenic pharmaceutical composition subsequently administered in terms of at least some physicochemical properties, such as size, shape and electrical charge, in a manner that induces cross-tolerization between desensitizing placebos and reactogenic particulate pharmaceutical compositions.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 3A shows the large pulmonary hypertensive reaction in pigs which followed a first i.v. bolus injection of 0.005 mg doxorubicin/kg of DOXIL™ (corresponding to 0.04 mg liposomal lipid/kg or 0.032 mg liposomal phospholipid/kg). FIG. 3B shows the lower pulmonary hypertensive reaction observed in the same animal after the second i.v. bolus injection of 0.01 mg doxorubicin/kg) of DOXIL™. FIG. 3C shows the pulmonary hypertensive reaction which followed an i.v. bolus injection of 0.5 mg/kg zymosan injected to the same animal after the second bolus injection of DOXIL™.

FIG. 8. In vitro complement activation by DOXIL™ and Doxebo in human serum estimated by S protein-bound C5b-9 (SC5b-9) increase.

DETAILED DESCRIPTION OF THE INVENTION

Figure 1:
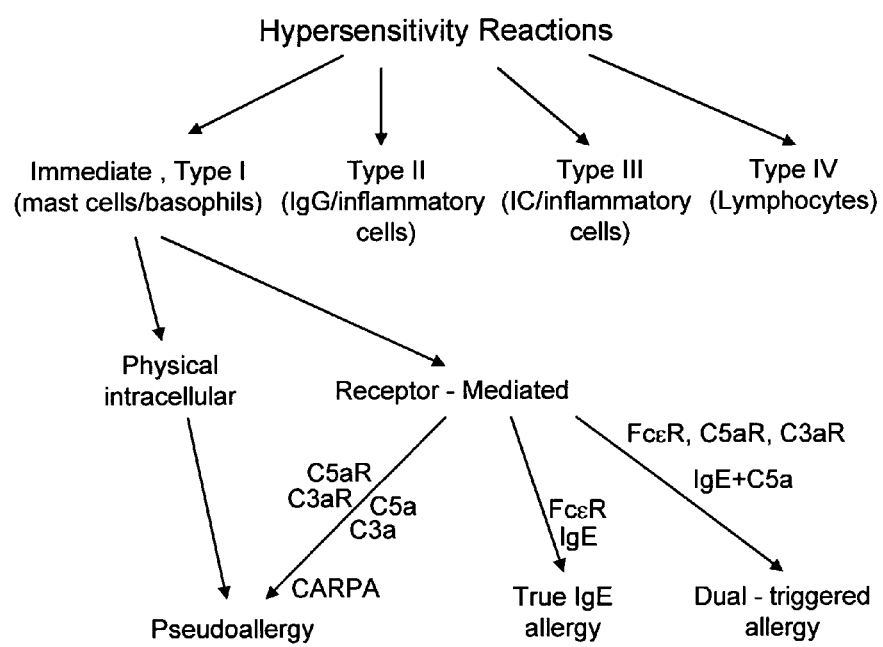
FIG. 1. A scheme representing the recently proposed reclassification of hypersensitivity reactions.

The present invention relates to the use of placebo drug carrier, including a drug free carrier or a carrier containing an active ingredient in subtherapeutic doses for preventing or reducing the unwanted symptoms of hypersensitivity reactions associated with the administration of a reactogenic pharmaceutical composition.

The present invention specifically provides methods for diminishing, preventing or treating hypersensitivity reactions associated with the administration of reactogenic pharmaceutical compositions. Particularly the present invention confer protection via densitization towards hypersensitivity reactions associated with the administration of reactogenic pharmaceutical compositions including vehicles or carriers that are particulate in nature.

The vehicles and carriers of the present invention may include liposomes, lipid micelles, lipoprotein micelles and polymeric micelles. Other carriers to be used according to present invention may include polymer nanoparticles, polymer microparticles, block copolymer micelles, lipid stabilized emulsions, polymer-lipid hybrid systems and derivatized single chain polymers and other linear, spherical or tubular polymers. The carriers may further include carbon or other nanotubes including linear and spherical, uni- and multiwalled nanotubes. The carriers may also include dendrimers, fullerenes, buckyballs, antibodies and proteins.

In certain embodiments, the carriers of the present invention are considered nanoparticles as they comprise molecular or nonmolecular assemblies in the nanometer range. Preferably, the size of the carriers ranges between 5 to 10,000 nm in diameter. More preferably the drug carriers have a mean diameter of between 5 and 500 nm. It is recognized that for intravenous administration the drug carriers are typically about 5-10,000 nm in diameter. Preferred drug carriers are about 5-500 nm in diameter, more preferably 5-200 nm in diameter. For inhalation, intra-thecal, intra-articular, intra-arterial, intra-peritonal or subcutaneous administration, carriers are typically from 4 μm to an excess of 50 μm. Pharmaceutical composition including carriers intended for intraocular administration are generally smaller (<4 μm).

The present invention provides methods for preventing or reducing the unwanted symptoms of hypersensitivity reactions associated with the administration of a reactogenic pharmaceutical composition including pretreatment by means of administering a placebo drug carrier prior to the administration of the reactogenic pharmaceutical composition, wherein the placebo drug carrier can be administered in two forms: a) as a drug-free carrier also referred to as an empty carrier and b) as a carrier including an active ingredient in subtherapeutic doses. In some embodiments the active ingredient of the placebo is the active ingredient found in the reactogenic pharmaceutical composition, in other embodiments, the active ingredient can be a derivative of the active ingredient found in the reactogenic pharmaceutical composition.

According to the present invention the placebo drug carrier is administered prior to the administration of the reactogenic pharmaceutical composition. According to one embodiment the term "prior" as used herein, may refer to a period of time immediately before a reactogenic pharmaceutical composition is administered to an individual. "Prior" in this respect may be used to indicate a time days, hours or minutes before the administration of a reactogenic pharmaceutical composition. According to another embodiment the term "prior" may refer to a period of time immediately before the reactogenic pharmaceutical composition enters into the blood circulation. "Prior" in this respect may be used to indicate a time of hours or minutes. The terms "administered", "administering" and "administration" as used herein, may refer according to one embodiment to the actual operation of giving the placebo drug carrier and the reactogenic pharmaceutical composition to an individual, according to another embodiment they may refer to the actual insertion of the placebo and pharmaceutical compositions into the blood circulation.

According to one embodiment the hypersensitivity reaction is an immediate hypersensitivity or type I allergy and comprise the complement system activation-related pseudoallergy (CARPA), according to another embodiment said hypersensitivity is manifested in a broad array of abnormal physiological conditions selected from anaphylaxis, anaphylactic reactions, anaphylactoid reactions, pseudoallergy, infusion reactions and idiosyncratic reactions wherein the associated symptoms may be acute or subacute and may vary from mild to severe, life threatening or even deadly.

The symptoms of hypersensitivity reactions in general and anaphylactic reaction in particular vary considerably among patients. Typically, in about 1 to 15 minutes (but rarely after as long as 2 hours), symptoms can include agitation and flushing, palpitations, paresthesias, pruritus, throbbing in the ears, chill, coughing, choking, sneezing, urticaria and angioedema, vasodilation, astma attack and difficulty breathing owing to laryngeal edema or bronchospasm. Confusion, conjunctivitis, cyanosis, dermatitis, diaphoresis, dyspnea, erythema, fever, headache, hypoxemia, low back pain, lumbar pain, metabolic acidosis, panic, rash, rhinitis, skin eruptions, tachypnea, tingling sensations, nausea, vomiting, abdominal pain, and diarrhea are also sometimes observed. Shock may develop within another 1 or 2 minutes, and the patient may convulse, become incontinent, unresponsive, and succumb to cardiac arrest, massive angioedema, hypovolemia, severe hypotension and vasomotor collapse and primary cardiovascular collapse. Death may ensue at this point if the antagonist epinephrine is not immediately available. Mild forms of anaphylactic response result in various symptoms including generalized pruritus, urticaria, angioedema, mild wheezing, nausea and vomiting.

An "individual who is at risk of having hypersensitivity reactions" according to the present invention is any individual who is about to be treated with a reactogenic pharmaceutical composition, specifically pharmaceutical compositions comprising particulate vehicles or carriers. Individuals with a greater risk of developing hypersensitivity reactions are those referred to as having atopy, or atopic constitution, or have known allergies to certain foods, pollens, animal danders or any other types or known allergens, or who have reacted previously to any drug or antigen with allergic reaction.

The term "drug free carrier" refers to an "empty" carrier which is a carrier lacking an active ingredient selected from a drug or a diagnostic agent.

As used herein, the term "subtherapeutic dose" means that the dosage or amount of the active ingredient (being a drug or a diagnostic agent) is insufficient to achieve the desired pharmacological action in the absence of other active ingredients. The subtherapeutic doses preferably consist of active ingredients in doses less than 20% of the intended therapeutic dose, more preferably less than 10% of the intended therapeutic dose, still more preferably less than 5% of the intended therapeutic dose, even more preferably less than 2% of the intended therapeutic dose or most preferably less than 1% of the intended therapeutic dose. In the present specification the term "subtherapeutic dose" may be referred to alternatively as "subnormal dose" or "subnormal level".

The term "reactogenic pharmaceutical composition" as used herein refers to a particulate pharmaceutical composition comprising at least one component capable of inducing hypersensitivity reactions which symptoms include but are not limited to the "symptoms of hypersensitivity reactions" described above. According to one preferred embodiment of the present invention the reactogenic particulate pharmaceutical composition comprises a vehicle or a carrier and an active ingredient.

The active agent may be any drug or diagnostic agent that can be carried in vehicles or carriers mentioned above such as liposomes or micelles including antifungal or anticancer drugs, regardless of their chemical nature, such as proteins, for example, hemoglobin, peptides, amino acids, carbohydrates, oligo and polynucleic acids or any type of organic or inorganic atoms or molecules.

Examples of active ingredients include but are not limited to: nirogenated mustard analogues like cyclophosphamide; melphalan; iphosphamide; or trophosphamide; ethylenimines like thiotepa; nitrosoureas like carmustine; alkylating agents like temozolomide; or dacarbazine; analogous antimetabolites of folic acid like methotrexate or raltitrexed; analogues of purines like thioguanine, cladribine or fludarabine; analogues of pyrimidines like fluorouracil, tegafur or gemcitabine; alkaloids of Vinca and analogues like vinblastine, vincristine or vinorelbine; derivatives of podophyllotoxin like etoposide, taxanes, docetaxel or paclitaxel; anthracyclines and similar like doxorubicin, daunorubicin, epirubicin, idarubicin and mitoxantrone; other cytotoxic antibiotics like bleomycin and mitomycin; platinum compounds like cisplatin, carboplatin and oxaliplatin; monoclonal antibodies like rituximab; other antineoplastic agents like pentostatin, miltefosine, estramustine, topotecan, irinotecan, c-raf antisense, CTP-11 and bicalutamide; antifungal agents like amphotericin B and photosensitizers like verteporfin. Examples for reactogenic pharmaceutical compositions considered according to the present invention are listed in the tables 1 and 2 describing liposome and lipid based drugs approved and in clinical development respectively:

TABLE 1

Marketed liposome- or lipid-based drugs

| Encapsulated drug | Trade name | Indications |
|---|---|---|
| Doxorubicin (Adriamycin) | DOXIL* CAELYX* MYOCET | Ovarian cancer, Kaposi's sarcoma, metastatic breast cancer, muliple myeloma |
| Daunorubicin | DAUNOXOME | advanced HIV-associated Kaposi's sarcoma |
| Amphotericin B | AMBIOSOME ABELCET AMPHOTEC | Systemic fungal infections |

*Doxil(USA) and Caelyx (Europe) are different names to the same product

TABLE 2

Other liposome- or lipid-based drugs either recently approved or in clinical development.

| Encapsulated drug | Trade name | Indications |
|---|---|---|
| Verteporfin | Visudyne | subfoveal neovascularization due to macular degeneration, pathologic myopia and ocular histoplasmosis |
| All-trans-retinoic acid (ATRA) | ATRA-IV | Non-Hodgkin lymphoma, acute promyelocytic leukaemia, etc. |
| Oxaliplatin | Aroplatin | Colorectal and other solid tumors |
| Vincristine | Onco TCS | Lymphoma, acute lymphoblastic leukaemia, Hodgkin's diseaselung cancer, pediatric malignancies |
| Topotecan | Topotecan TCS* | Various cancers |
| Vinorelbine | Vinorelbine TCS* | Various cancers |
| Doxorubicin | LED | Advanced cancers, including breast |
| Paclitaxel | LEP-ETU | Advanced cancers, including breast, lung and ovarian |
| Mitoxantrone | LEM-ETU | Advanced cancers, including prostate |
| c-raf antisense oligonucleotide | LErafAON | Advanced cancers, including pancreatic |
| CPT-11 (irinotecan, Camptosar ™) | LE-SN38 | Advanced cancers, including colorectal and lung |

*TCS, Transmembrane Carrier System

The drug vehicles or carriers of the present invention may include liposomes, lipid micelles, lipoprotein micelles, polymeric micelles, lipid stabilized emulsions, polymer nanoparticles, polymer microparticles, block copolymer micelles, polymer-lipid hybrid systems, derivatized single chain polymers, and the like.

Liposome Compositions:

Liposomes for use in this invention may be prepared to include liposome-forming phospholipids, membrane active sterols (cholesterol) and lipopolymers. Liposome-forming lipids are mainly glycerophopshilipids ans sphingomelins. The glycerophopsholipids include lipids having a glycerol backbone wherein at least one, preferably two, of the hydroxyl groups at the head group is substituted by one or two of an acyl, an alkyl or alkenyl chain, a phosphate group, preferably an acyl chain (to form an acyl or diacyl derivative), a combination of any of the above, and/or derivatives of same, and may contain a chemically reactive group (such as an amine, acid, ester, aldehyde or alcohol) at the headgroup, thereby providing a polar head group. The sphingomyelins have two hydrocarbon chains one is an acyl chain covalently bound to the primary amino group of the long chain amino alcohol sphingosine who contribute the second long hydrocarbon chain. Phosphocholine attached by a phosphoester to the C1 hydroxyl group of the sphingosine contribute the polar head group of the sphingomyelin (which is identical to this of phopshatidylcholine).

The liposome forming lipids are typically, 14-24 carbon atoms in length, and have varying degrees of saturation, thus resulting in fully, partially or non-hydrogenated liposome-forming lipids. The lipids may be of a natural source, semi-synthetic or fully synthetic lipids, and may be neutral, negatively or positively charged. There are a variety of synthetic liposome forming lipids and naturally-occurring liposome forming lipids, including phospholipids, such as phosphatidylcholine (PC), phosphatidylinositol (PI), phosphatidylglycerol (PG), dimyristoyl phosphatidylglycerol (DMPG), egg yolk phosphatidylcholine (EPC), 1-palmitoyl-2-oleoylphosphatidyl choline (POPC), hydrogenated soy phosphatidylcholine (HSPC), distearoylphosphatidylcholine (DSPC), dimyristoyl phosphatidylcholine (DMPC); phosphatidic acid (PA), phosphatidylserine (PS); 1-palmitoyl-2-oleoylphosphatidyl choline (POPC), and the sphingophospholipids such as sphingomyelins (SM) including N-stearoyl sphingomyelin, or N-palmitoyl sphingomyelin. The above-described lipids and phospholipids can be obtained commercially or prepared according to published methods in the art. Other suitable liposome-forming lipids include glyceroglycolipids, sphingoglycolipids and sterols (such as cholesterol or plant sterol).

The liposome-forming lipids can be in the form of zwitterionic phospholipids wherein for example the cationic and anionic moieties have identical number of charges (constituting the head group) all remain fully ionized over a broad pH range with no net charge (zeta potential=~0 mV; Barenholz and Cevc, 2000). Cationic lipids (mono- and polycationic) may also be used to form liposomes either as an individual component or wherein the cationic lipid is included as a minor/major component of the lipid composition. Such cationic lipids typically have a lipophilic moiety, such as a sterol, an acyl or diacyl chain, and where the lipid has an overall net positive charge. Cationic lipid species include, but are not limited to: 3.beta.[.sup.4N-(.sup.1N.sup.8N-diguanidino spermidine)-carbamoyl] cholesterol (BGSC); 3.beta.[N,N-diguanidinoethyl-aminoethane)-carbamoyl] cholesterol (BGTC); N,N.sup.1,N.sup.2,N.sup.3 Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2(sperminecarboxamido)ethyl]-N,N-dimethyl-1-p-ropanaminium trifluoroc-etate) (DOSPA); 1,3-dioleoyloxy-2-(6-carboxyspermyl)-propyl amide (DOSPER); polycationic sphingolipid ceramide carbamoyl spermine (CCS),4-(2,3-bis-palmitoyloxy-propyl)-1-methyl-1H-imidazole (DPIM) N,N,N',N'-tetramethyl-N,N'-bis(2-hydroxyethyl)-2,3dioleoyloxy-1,4-butaned-iammonium iodide) (Tfx-50); 1,2 bis(oleoyloxy)-3-(trimethylammonio) propane (DOTAP); N-1-(2,3-dioleoyloxy) propyl-N,N,N-trimethyl ammonium chloride (DOTMA) or other N—(N,N-1-dialkoxy)-alkyl-N,N,N-trisubstituted ammonium surfactants; 1,2dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DOR1 (DL-1,2-dioleoyl-3-dimethylaminopropyl-.beta.-hydroxyethylammonium) or DORIE (DL-1,2-O-dioleoyl-3-dimethylaminopropyl-.beta.-hydroxyethylammonium) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspemmine (DPPES) or the cationic lipids disclosed in U.S. Pat. No. 5,283,185, cholesteryl-3.beta.-carboxyl-amido-ethylenetrimethyl-ammonium iodide, 1-dimethylamino-3-trimethylammonio-DL-2-propyl-cholesteryl carboxylate iodide, cholesteryl-3.beta.-carboxyamidoethyleneamine, cholesteryl-3.beta.-oxysuccinamido-ethylenetrimethylammonium iodide, 1-dimethylamino-3-trimethylammonio-DL-2-propyl-cholesteryl-3.beta.-oxysuc-cinate iodide, 2-(2-trimethylammonio)-ethylmethylamino ethyl-cholesteryl-3.beta.-oxysuccinate iodide, 3.beta.N—(N',N'-dimethylaminoethane) carbamoyl cholesterol (DC-chol), and 3.beta.—N-(polyethyleneimine)-carbamoylcholesterol.

The liposomes may also include a lipid derivatized with a polymer to form new entities known by the term lipopolymers. Lipopolymers preferably comprise lipids modified at their head group with a polymer having a molecular weight equal to or above 750 Da. The head group may be polar or apolar; however, it is preferably a polar head group to which a large (>750 Da), highly hydrated (at least 60 molecules of water per head group), flexible polymer is attached. The hydrophilic polymer head group may be attached to the lipid region covalently or non-covalently; however, it is preferably attached via the formation of a covalent bond (optionally via a linker). The outermost surface coating of the hydrophilic polymer chains is effective to provide a liposome with a long blood circulation lifetime in vivo.

Liposomes may include other phopsholipids which are not liposome forming lipids, such as phosphatidylethanolamines and their hydrophilic polymer derivatives. The lipopolymers may be non-ionic lipopolymers (also referred to as neutral lipopolymers or uncharged lipopolymers) or lipopolymers having a net negative or positive charge. There are numerous polymers which may be attached to lipids. Polymers typically used as lipid modifiers include, but not limited to: polyethylene glycol (PEG), polysialic acid, polylactic acid (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers. While the lipids derivatized into lipopolymers may be neutral, negatively charged, or positively charged, the most commonly used and commercially available lipids derivatized into lipopolymers are those based on phosphatidyl ethanolamine (PE), usually, distearylphosphatidylethanolamine (DSPE). A specific family of lipopolymers which may be employed by the invention include monomethylated PEG attached to DSPE (with different lengths of PEG chains, the methylated PEG referred to herein by the abbreviation PEG) in which the PEG polymer is linked to the lipid via a carbamate linkage resulting in a negatively charged lipopolymer. Other lipopolymers are the neutral methyl polyethyleneglycol distearoylglycerol (mPEG-DSG) and the neutral methyl polyethyleneglycol oxycarbonyl-3-amino-1,2-propanediol distearoylester (mPEG-DS) (Garbuzenko et al., 2005). The PEG moiety preferably has a molecular weight from about 350 Da to about 100,000 Da. More preferably, the molecular weight is from about 350 Da to about 20,000 Da, more preferably, the molecular weight is from about 750 Da to about 12,000 Da and it is most preferably between about 1,000 Da to about 5,000 Da.

All amphiphiles including all lipids are characterized by a geometric parameter referred to as packing parameter which is the ratio of cross section of their hydrophobic region divided by the cross section of their hydrophilic region (Barenholz and Cevc 2000). Lipsome forming lipids have a packaging parameter of 0.74-1.0. For micelle forming lipids like PEG-DSPE this parameter is lower than 0.74 while for lipids which favor inverted phases such Hexagonal type II phase the packing parameter is higher than 1.0. In order to obtain stable liposomes the additive packing parameter (which is the mole % weighted average packing parameter) should be in the range of 0.74 to 1.0.

Lipids may also contain lipid protective agents, such as, but not limited to, α-tocopherol, α-tocopherol acetate, or α-tocopherol succinate to protect the lipid components against free radical damage. Typically such agents are included at a mole percentage in the range of 0.5-2%. In certain instances it is advantageous to add α-tocopherol to the liposomes to maintain a balance between vitamin E and polysaturated lipids in the liposomes.

Preparations of Liposomes:

Liposomes can be prepared as described in Janoff A. S. (1999), or by additional techniques known to those knowledgeable in the art. Different types of liposomes may be employed in the context of the present invention, including, but not limited to, large multilamellar vesicles (MLV), small unilamellar vesicles (SUV), large unilamellar vesicles (LUV), sterically stabilized liposomes (SSL), multivesicular vesicles (MVV), and large multivesicular vesicles (LMVV). "Large" refers to liposomal sizes above 100 nm, however in most cases the multilamellar liposomes and multivesicular liposomes are in the micrometer size range.

A variety of methods for producing liposomes are available and have been reviewed in Szoka (1980). In general these methods are used to prepare liposomes having heterogeneous sizes of 0.02-20 μm. A general method for producing liposome suspension involves placing vesicle-forming lipids in a suitable organic solvent system, followed by drying under vacuum or under an inert gas to form a lipid film in a vessel. An aqueous suspension medium, such as a sterile saline solution, is then added to the film, and the vessel is agitated until the lipids have hydrated to completion, typically within 1-2 hours. The amount of aqueous medium added is such as to produce a final liposome suspension containing preferably between about 10 and 30 g lipid per 100 ml media.

The formation of multilamellar vesicles (MLVs) can be obtained by subsequent hydration of the lipids to form vesicles of sizes ranging between about 0.5 microns to about 10 microns or larger. In general, the size distribution of MLVs can be shifted toward slightly smaller sizes by hydrating the lipids under vigorous shaking conditions.

MLV may be alternatively prepared by: (a) vortexing a lipid film with an aqueous solution, such as a solution of ammonium sulfate; (b) homogenizing the resulting suspension to form a suspension of small unilamellar vesicles (SUV); and (c) repeatedly freeze-thawing said suspension of SUV in liquid nitrogen followed by thawing in a water bath (37° C.). Preferably, the freeze-thawing procedure is repeated at least five times. The extraliposomal ammonium sulfate is then removed, preferentially by dialysis against normal saline.

The aqueous medium used in forming the liposomes may contain a water-soluble agent (eg. iron-specific trihydroxamine chelating agent) to enhance the stability of the liposomes upon storage. These compounds are used to reduce lipid peroxidation and free radical damage in drug-containing liposomes (U.S. Pat. No. 4,797,285). Typically, a chelator concentration of between about 10-200 micromolar is sufficient.

Lipopolymers may be introduced into the liposome in two different ways either by: (a) the more commonly used way of adding the lipopolymer to a lipid mixture prior to lipid hydration, thereby forming the liposome, where the lipopolymer will be incorporated and exposed at the inner and outer leaflets of the liposome bilayer; or (b) first preparing the liposome and then incorporating the lipopolymers into the external leaflet of the pre-formed liposome either by incubation at a temperature above the Tm of the lipopolymer and liposome-forming lipids (Uster et al., 1996), or by short-term exposure to microwave irradiation (WO/2006/042270). In order to produce a desired liposome size and size homogeneity the liposome suspension may be subjected to ultrasonic irradiation, homogenization or extrusion procedures. Ultrasonic irradiation in an ultrasonic bath or probe sonication leads to a progressive size reduction down to small unilamellar vesicles (SUVs) of sizes ranging between about 20-100 nm (20 nm is the smallest size a liposome can reach). Another method for fragmenting large liposomes into smaller ones uses high pressure homogenization which relies on shearing energy. In a typical homogenization procedure, MLVs are recirculated through a standard emulsion homogenizer until selected liposome sizes, typically less than 100 nm, are obtained. Extrusion of liposomes through a small-pore polycarbonate membrane is an effective method for reducing liposome size down to a relatively well-defined size distribution. An average range is between about 0.03 and 1 micron, depending on the pore size of the membrane. Typically, the suspension is cycled through the membrane several times (using membranes of decreasing pore sizes) until the desired liposome size distribution is achieved. The liposomes extrusion through successively smaller-pore membranes, enables a gradual reduction in liposome size down to the desired size.

The down-sized processed liposome suspension may be readily sterilized by passage through a sterilizing membrane having a particle discrimination size of about 0.2 microns, such as a conventional 0.22 micron depth membrane filter. If desired, the liposome suspension can be lyophilized in the presence of a suitable cryoprotectant for storage and reconstituted by hydration shortly before use.

Another approach for the preparation of liposomes is disclosed in PCT publication WO 2007/049279 (incorporated herein by reference) and includes mixing dry liposome constituents, such as liposome-forming lipids, cholesterol, etc.; solvating or dissolving the mixture in an aprotic organic solvent which is miscible in water, such as ethanol; and adding to the dissolved/solvated mixture a solution comprising a salt (pH forming aqueous solution to obtain a liposome suspension having an amount of the organic solvent in the final volume (may even be up to 25% of the organic solvent from final volume). Using this approach, typically MLVs of sizes between 0.3 μm and 5 μm. are formed.

Other Vehicles or Carriers:

Micelles are self-assembled particles composed of amphiphiles having a packing parameter smaller than 0.74 or polymeric components that are utilized for the delivery of sparingly soluble agents present in the hydrophobic core. Various means for the preparation of micellar particulate carriers are available and may be carried out with ease by one skilled in the art. For instance, lipid micelles may be prepared as described in Perkins, et al., 2000) (incorporated herein by reference). Lipoprotein micelles can be prepared from natural or artificial lipoproteins including low and high-density lipoproteins and chylomicrons. Polar lipid-stabilized emulsions are micelles prepared such that they comprise an oil (neutral lipid) droplet filled core stabilized by an emulsifying component such as a monolayer of polar lipids. The core may comprise fatty acid esters such as—triacylglycerol (i.e. long chain and medium chain triaclglycerols), cholesterol esters, squalane and alike). The monolayer may comprise of liposome forming lipids (such as PCs) without or with micelle forming lipids (such as Lyso PC, a hydrophilic polymer lipid conjugate such as DSPE-PEG) and inverted phase forming lipids (such as PE). These emulsions may be prepared by homogenization of the oil in the presence of the polar lipids. Synthetic polymer analogues that display properties similar to lipoproteins such as micelles of stearic acid esters or poly (ethylene oxide) block-poly(hydroxyethyl-L-aspartamide) and poly(ethylene oxide)-block-poly(hydroxyhexyl-L-aspartamide) may also be used in the practice of this invention (Lavasanifar, et al., 2000).

Nanoparticles and microparticles may comprise a concentrated core of drug that is surrounded by a polymeric shell (nanocapsules) or as a solid or a liquid dispersed throughout a polymer matrix (nanospheres). General methods of preparing nanoparticles and microparticles are described by Soppimath, et al. 2001), the reference of which is incorporated herein. Other polymeric particulate carriers that may be used include block copolymer micelles; they are generally utilized as carriers for hydrophobic drugs and can be prepared as found in Allen, et al., 1999). Polymer-lipid hybrid systems consist of a polymer nanoparticle surrounded by a lipid monolayer. The polymer particle serves as a cargo space for the incorporation of hydrophobic drugs while the lipid monolayer provides a stabilizing interference between the hydrophobic core and the external aqueous environment. Polymers such as polycaprolactone and poly(d,1-lactide) may be used while the lipid monolayer is typically composed of a mixture of lipid. Suitable methods of preparation are similar to those referenced above for polymer nanoparticles. Derivetized single chain polymers are polymers adapted for covalent linkage of a biologically active agent to form a polymer-drug conjugate. Numerous polymers have been proposed for synthesis of polymer-drug conjugates including polyaminoacids, a polysaccharides such as dextrin or dextran, and synthetic polymers such as N-(2-hydroxypropyl)methacrylamide (HPMA) copolymer. Suitable methods of preparation are detailed in Veronese and Morpurgo, 1999).

Preparation of Vehicles and Carriers Containing Subtherapeutic Doses of an Active Ingredient:

The active ingredients are "encapsulated" in the vehicles or carriers. "Encapsulation", as used herein, includes covalent or non-covalent association of an active ingredient or agent with the vehicle or carrier. For example, this can be by interaction of the agent with the outer layer or layers of the vehicle or carrier or entrapment of an agent within the vehicle or carrier, equilibrium being achieved between different portions of the vehicle or carrier. For example, for liposomes, encapsulation of an agent can be by association of the agent by interaction with the bilayer of the liposomes through covalent or noncovalent interaction with the lipid components or entrapment in the aqueous interior of the liposome, or in equilibrium between the internal aqueous phase and the bilayer. For polymer-based vehicles or carriers, encapsulation can refer to covalent linkage of an agent to a linear or non-linear polymer. Further, non-limiting examples include the dispersion of agent throughout a polymer matrix, or the concentration of drug in the core of a nanocapsule, a block copolymer micelle or a polymer-lipid hybrid system. "Loading" refers to the act of encapsulating an agent into a vehicle or carrier.

Means of altering release rates and improving drug retention include rigidifying the liposome membrane and reducing its free volume by increasing the acyl-chain length and saturation of liposome forming lipids (PC and SM), controlling the exchange of surface grafted hydrophilic polymers such as PEG out of the liposome membrane and incorporating membrane-rigidifying agents such as sterols into the membrane.

Techniques for encapsulation are dependent on the nature of the vehicles or carriers. For example, therapeutic agents may be loaded into liposomes using both passive and active loading methods.

Passive methods of encapsulating agents in liposomes involve encapsulating the agent during the preparation of the liposomes. In this method, the drug may be membrane associated or encapsulated within an entrapped aqueous space. This includes a passive entrapment method described by Bangham, et al., (1965), where the aqueous phase containing the agent of interest is put into contact with a film of dried vesicle-forming lipids deposited on the walls of a reaction vessel. Upon agitation by mechanical means, swelling of the lipids will occur and multilamellar vesicles (MLV) will form. Using extrusion, the MLVs can be converted to large unilamellar vesicles (LUV) or small unilamellar vesicles (SUV). Another method of passive loading that may be used includes that described by Deamer and Bangham, (1976). This method involves dissolving vesicle-forming lipids in ether and, instead of first evaporating the ether to form a thin film on a surface, this film being thereafter put into contact with an aqueous phase to be encapsulated, the ether solution is directly injected into said aqueous phase and the ether is evaporated afterwards, whereby liposomes with encapsulated agents are obtained. A further method that may be employed is the Reverse Phase Evaporation (REV) method described by Szoka and Papahadjopoulos, (1978), in which a solution of lipids in a water insoluble organic solvent is emulsified in an aqueous carrier phase and the organic solvent is subsequently removed under reduced pressure.

Other methods of passive entrapment that may be used include subjecting liposomes to successive dehydration and rehydration treatment, or freezing and thawing. Dehydration is carried out by evaporation or freeze-drying. This technique is disclosed by Kirby, et al., (1984). Also, Shew and Deamer (1985), describe a method wherein liposomes prepared by sonication are mixed in aqueous solution with the solute to be encapsulated, and the mixture is dried under nitrogen in a rotating flask. Upon rehydration, large liposomes are produced in which a significant fraction of the solute has been encapsulated.

The loading may be improved by co-lyophilizing the agent with the lipid sample and rehydrating in the minimal volume allowed to solubilize the agent. The solubility may be improved by varying the pH of the buffer, increasing temperature or addition or removal of salts from the buffer.

Active encapsulation methods may also be used. For example, liposomes may be loaded according to a metal-complexation or ion gradient or pH gradient loading techniques. With pH gradient loading, liposomes are formed which encapsulate an aqueous phase of a selected pH. Hydrated liposomes are placed in an aqueous environment of a different pH selected to remove or minimize a charge on the drug or other agent to be encapsulated.

Once the agent moves inside the liposome, the pH of the interior results in a charged agent state, which prevents the agent from permeating the lipid bilayer, thereby entrapping the agent in the liposome.

To create a pH gradient, the original external medium can be replaced by a new external medium having a different concentration of protons. The replacement of the external medium can be accomplished by various techniques, such as, by passing the lipid vesicle preparation through a gel filtration column, e.g., a Sephadex G-50 column, which has been equilibrated with the new medium (as set forth in the examples below), or by centrifugation, dialysis, or related techniques. The internal medium may be either acidic or basic with respect to the external medium.

After establishment of a pH gradient, a pH gradient loadable agent is added to the mixture and encapsulation of the agent in the liposome occurs as described above.

Loading using a pH gradient may be carried out according to methods described in U.S. Pat. Nos. 5,616,341, 5,736,155 and 5,785,987 incorporated herein by reference. A preferred method of pH gradient loading is the citrate-based loading method utilizing citrate as the internal buffer at a pH of 2-6 and a neutral external buffer.

Various methods may be employed to establish and maintain a pH gradient across a liposome all of which are incorporated herein by reference. This may involve the use of ionophores that can insert into the liposome membrane and transportions across membranes in exchange for protons (see for example U.S. Pat. No. 5,837,282).

The loading of doxorubicin (e.g., DOXIL™) into the preformed lipo is driven by transmembrane ammonium sulfate gradient (U.S. Pat. No. 5,192,549, U.S. Pat. No. 5,316,771 and Haran et al., 1993).

Compounds encapsulated in the interior of the liposome that are able to shuttle protons across the liposomal membrane and thus set up a pH gradient (see for example U.S. Pat. No. 5,837,282) may also be utilized. These compounds comprise an ionizable moiety that is neutral when deprotonated and charged when protonated. The neutral deprotonated form (which is in equilibrium with the protonated form) is able to cross the liposome membrane and thus leave a proton behind in the interior of the liposome and thereby cause an decrease in the pH of the interior. Examples of such compounds include methylammonium chloride, methylammonium sulfate, ethylenediammonium sulfate (see U.S. Pat. No. 5,785,987) and ammonium sulfate. Internal loading buffers that are able to establish a basic internal pH, can also be utilized. In this case, the neutral form is protonated such that protons are shuttled out of the liposome interior to establish a basic interior. An example of such a compound is calcium acetate (see U.S. Pat. No. 5,939,096).

Metal-based active loading typically uses liposomes with passively encapsulated metal ions (with or without passively loaded therapeutic agents). Various salts of metal ions are used, presuming that the salt is pharmaceutically acceptable and soluble in an aqueous solutions. Actively loaded agents are selected based on being capable of forming a complex with a metal ion and thus being retained when so complexed within the liposome, yet capable of loading into a liposome when not complexed to metal ions.

Agents that are capable of coordinating with a metal typically comprise coordination sites such as amines, carbonyl groups, ethers, ketones, acyl groups, acetylenes, olefins, thiols, hydroxyl or halide groups or other suitable groups capable of donating electrons to the metal ion thereby forming a complex with the metal ion. Examples of active agents which bind metals include, but are not limited to, quinolones such as fluoroquinolones; quinolones such as nalidixic acid; anthracyclines such as doxorubicin, daunorubicin and idarubicin; amino glycosides such as kanamycin; and other antibiotics such as bleomycin, mitomycin C and tetracycline; and nitrogen mustards such as cyclophosphamide, thiosemicarbazones, indomethacin and nitroprusside; camptothecins such as topotecan, irinotecan, lurtotecan, 9-aminocamptothecin, 9-nitrocamptothecin and 10-hydroxycamptothecin; and podophyllotoxins such as etoposide. Uptake of an agent may be established by incubation of the mixture at a suitable temperature after addition of the agent to the external medium. Depending on the composition of the liposome, temperature and pH of the internal medium, and chemical nature of the agent, uptake of the agent may occur over a time period of minutes or hours. Methods of determining whether coordination occurs between an agent and a metal within a liposome include spectrophotometric analysis and other conventional techniques well known to those of skill in the art.

Furthermore, liposome loading efficiency and retention properties using metal-based procedures carried out in the absence of an ionophore in the liposome are dependent on the metal employed and the lipid composition of the liposome. By selecting lipid composition and a metal, loading or retention properties can be tailored to achieve a desired loading or release of a selected agent from a liposome.

Amphipathic weak acids can be loaded into liposomes using preformed liposomes having a transmembrane calcium acetate gradient (U.S. Pat. No. 5,939,096, Clerc and Barenholz, 1995 and Avnir et al., 2008).

The Placebo compositions of the present invention may be used to treat hypersensitivity reactions in mammals. Thus, suitable subjects for treatment according to the methods and compositions of the invention include humans and mammals such as livestock or domestic animals and laboratory animals for research use.

As mentioned above, the Placebo compositions of the present invention may be administered to mammals, including humans. For treatment of human ailments, a qualified physician will determine how the compositions of the present invention should be utilized with respect to dose, schedule and route of administration using established protocols.

Preferably, the Placebo compositions of the present invention are administered parenterally, i.e., intraarterialy, intravenously, intraperitonealy, subcutaneously, or intramuscularly. More preferably, the Placebo compositions are administered intravenously, intraperitonealy by a bolus injection or by slow infusion or subcutaneously by bolus injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578.

Placebo compositions of the invention are prepared according to standard techniques and may comprise water, buffered water, 0.9% saline, 0.3% glycine, 5% dextrose and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, glucose, sucrose and the like.

Additionally, the placebo compositions may include lipid-protective agents which protect lipids against free-radical and lipid-peroxidative damages on storage. Lipophilic free-radical quenchers, such as alpha-tocopherol and water-soluble iron-specific chelators, such as EGTA or ferrioxamine, are suitable.

The concentration of vehicle or carrier in the placebo compositions can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, drug carriers composed of irritating lipids may be diluted to low concentrations to lessen inflammation at the site of administration. For diagnosis, the amount of carriers administered will depend upon the particular label used, the disease state being diagnosed and the judgment of the clinician.

Preferably, the placebo compositions of the present invention are administered intravenously. Dosage for the placebo compositions will depend on the administrating physician's opinion based on age, weight, and condition of the patient.

The principles of the present invention are demonstrated by means of the following non-limitative examples.

EXAMPLES

Example 1

A Model for Testing Liposomal C Activation-Related Pseudoallergy

The desensitization process resulted from the pretreatment with drug-free vehicle is demonstrated using the porcine model of liposomal C activation-related pseudoallergy (CARPA), and ELISA measurements of SC5b-9 (the terminal complement complex of C5b through C9 containing the serum S-protein) in human serum. The porcine model provides a particularly useful model to study liposome reactions, as practically all pigs develop major cardiopulmonary distress following intravenous injection of minute amounts (5-10 mg) of liposomes, corresponding to the sensitivity of those 2-7% of humans who develop severe hypersensitivity reactions to liposomal drugs (Szebeni et al., 2000a; Szebeni et al., 2007; Szebeni et al., 2002; Szebeni et al., 1999). The manifestations of the reaction, demonstrated in FIG. 2, include a rise of pulmonary arterial pressure (PAP), fall of cardiac output (CO) and $pCO_2$ in exhaled breath and rise or fall of systemic arterial pressure (SAP), along with major ECG abnormalities. These represent physiological changes that reasonably explain the human symptoms (dyspnea, chest pain, back pain, dizziness, panic). These symptoms are essentially common in administration of a variety of multilamellar vesicles with and without protein (hemoglobin) inside the vesicles (Szebeni et al., 2000a; Szebeni et al., 1999), DOXIL™ (Szebeni et al., 2006), the $^{99m}$Tc-chelator (HYNIC-PE)-containing pegylated small unilamellar liposomes (Szebeni et al., 2002) and AMBISOME™.

Figure 2A:
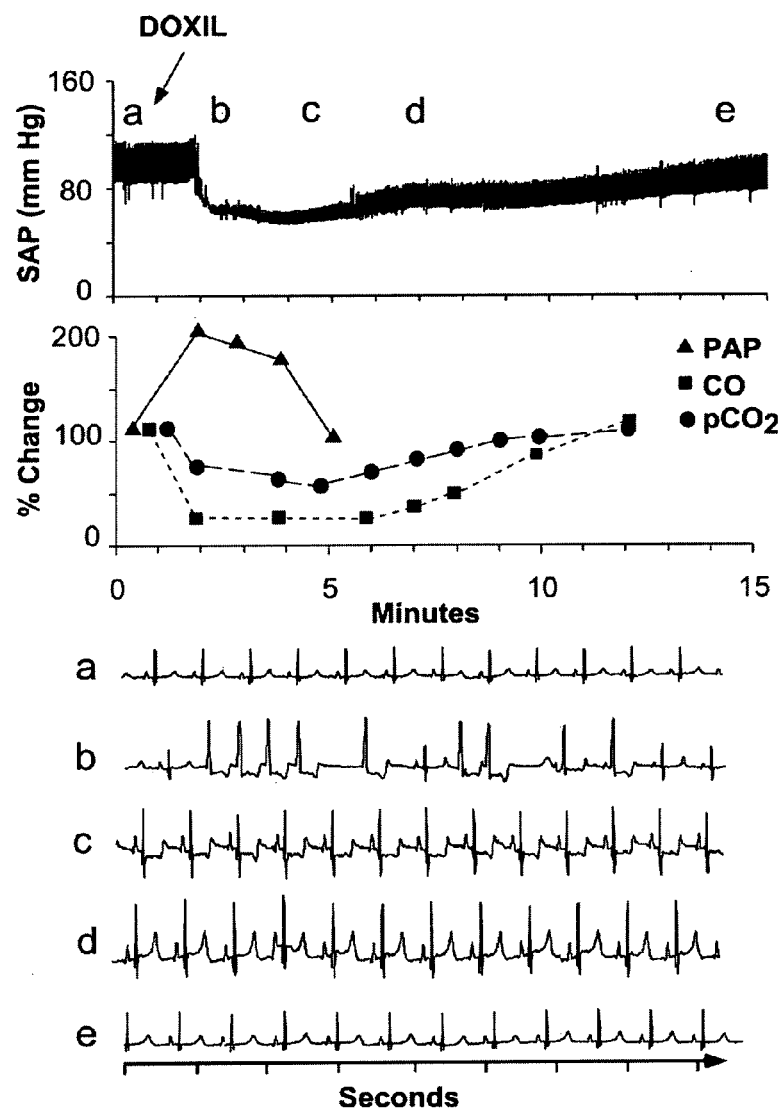
FIGS. 2A-2C. Variable manifestations of liposome-induced hypersensitivity in pigs. The figure shows typical cardiac electric (ECG) and systemic hemodynamic changes that followed the injection of increasing doses of liposomes in 3 different pigs (2A-2C) (Szebeni et al., 2006).
Figure 2B:
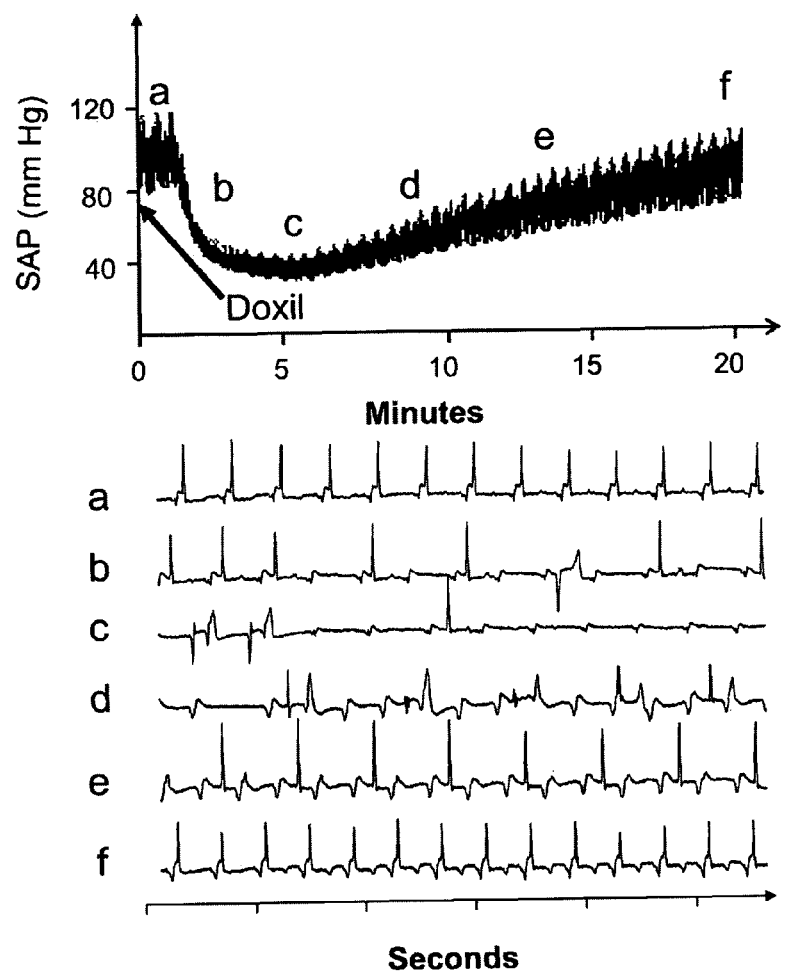
Figure 2C:
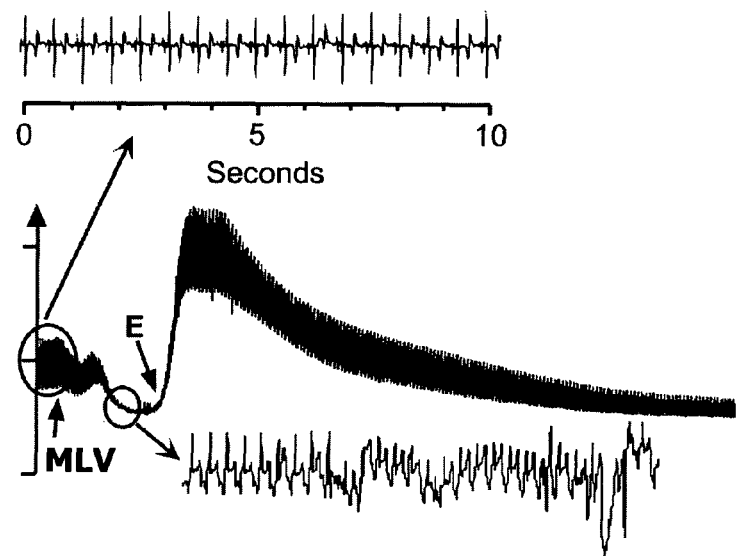
Figure 2C:
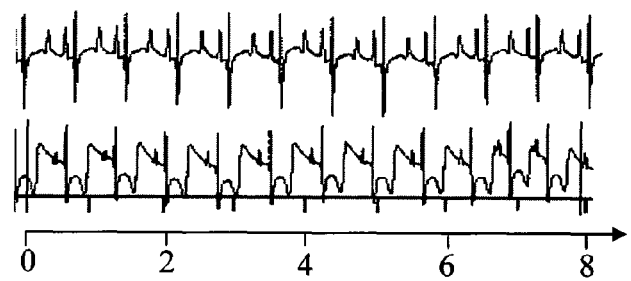

The type and dose of liposome administered determine the severity of the reaction, with 400-600% rise in pulmonary arterial pressure (PAP) relative to the baseline (from 8-12 mmHg to 40-50 mmHg), 20-80% fall in cardiac output (CO) and $pCO_2$ in exhaled breath, and major ECG abnormalities (Szebeni et al., 2006) (FIG. 2A). The quantitative nature of the PAP changes was also demonstrated by the linear relationship between liposome dose and sub-maximal rises of PAP (Szebeni et al., 1999) whereas its specificity to C activation became evident from the observations that small unilamellar liposomes, which had negligible C activating effect in vitro, also failed to cause hemodynamic changes in vivo (Szebeni et al., 2000a). Another observation further supporting the specificity to C activation stems from non-liposomal C activators (zymosan, xenogeneic immunoglobulins) which were shown to induce pulmonary pressure changes indistinguishable from those caused by large multilamellar liposomes (Szebeni et al., 2000a; 1999). In sum, previous experiments with the porcine liposome-induced cardiopulmonary distress model showed PAP to be the most accurate, sensitive and consistent clinical endpoint for assessing C activation-related pseudoallergy. The test can be qualified as a "large animal bioassay" for liposomal CARPA (Szebeni et al., 2000a; 2007; 2006; 2002; 1999).

The various features of liposome-induced hypersensitivity in pigs are demonstrated in FIG. 2. The figure shows typical cardiac and systemic hemodynamic changes that follow the injection of increasing doses of liposomes in 3 different pigs (2A-2C) (Szebeni et al., 2006). In 2A, injection of DOXIL™ lead to abrupt drop of mean arterial blood pressure (upper panel) that was associated with massive pulmonary hypertension decreased CO and decreased $pCO_2$ (middle panel). During the nadir of blood pressure curve, lasting for about 4 minutes, the transient tachyarrhythmic episode was followed by ST depression and T wave elevation (lower panel, curves b-d, respectively). Although the mean arterial blood pressure did not completely return to baseline, the ECG normalized after about 12-15 minutes (curve e). FIG. 2B presents a more severe reaction to a higher dose of DOXIL™, involving a deeper and longer hypotensive period compared to FIG. 2A. This reaction was associated with severe bradycardia, arrhythmia, and the presence of incomplete as well as complete AV blocks with asystole (FIG. 2B). Curves b-d in the lower panel of this figure show gradual increase of PQ interval leading to 2:1 AV block, suggesting that the bradycardia was not of sinus origin but rather a reflection of slowed AV conduction. FIG. 2C illustrates a lethal reaction involving ventricular fibrillation and cardiac arrest within 3 minutes after the injection of MLV. Resuscitation of this animal with epinephrine is also documented as a sudden overshoot of mean arterial blood pressure into the hypertension range. Additional notable features of hypotensive liposome reaction shown in FIGS. 2A-2C include a greater reduction of systolic pressure compared to diastolic pressure, resulting in a substantial reduction of pulse pressure amplitude. Furthermore, as illustrated in FIG. 2B, hypotension was often associated with bradycardia or bradyarrhythmia, although the physiological baroreflex response to hypotension is tachycardia. Hence, the phenomenon represents "relative", or "paradoxical" bradycardia (Szebeni et al., 2006).

Example 2

Tolerance Induction for DOXIL™ Associated Hypersensitivity Reactions by Repetitive Administration of the Drug DOXIL™ was obtained from the pharmacy of Semmelweis University, and contained doxorubicin HCl (2 mg/mL, 4.22 mM), HSPC (9.58 mg/mL), Chol (3.19 mg/mL), N-Carbamyl-poly(ethylene glycol methyl ether)-1,2-distearoyl-sn-glycerol-3-phospho-ethanol-amine triethyl ammonium salt with a polyethylene glycol (PEG) moiety of 2000 Da (2K-PEG-DSPE), 3.19 mg/mL), ammonium sulfate, mg/mL; 10 mM histidine (pH 6.5) and 10% sucrose. Dalant Mangalica pigs of both genders, weighing in the range of 21-30 kg, were sedated by intramuscular (i.m.) administration of ketamine, followed by intravenous (i.v.) administration of xylasine/ketamine-HCl (Calypsol) and Nembutal via the ear vein. Fluid (Salsol A or Ringer) supply maintaining circulatory stability was also provided via the ear vein. Ventilation was assisted by a Harvard ventilator (Harvard Apparatus, Cambridge, Mass.). Surgery was performed to cannulate the right int. jugular vein for drug injections and placing the Schwann-Ganz catether in wedge position in the right pulmonary artery to measure pulmonary arterial pressure (PAP). The right femoral artery was also cannulated for blood sampling and to measure systemic arterial pressure (SAP). The ECG was traced at the standard 3-lead detection points. Monitoring of hemodynamic parameters (PAP, SAP) heart rate and ECG started 3-5 minutes before the injections and continued until all hemodynamic parameters returned to baseline, usually within 15-25 minutes. Then, baseline monitoring was started for the next injection. Additional endpoints of hypersensitivity reactions included blood cell (leukocyte and platelet) counts and measurement of thromboxane B2 in blood. To obtain blood for these measurements, 5 to 10 mL blood samples were taken from the femoral artery into heparinized tubes before each injection (baseline), and at the top of liposome reactions, usually between 4-10 minutes after the injections. Blood was centrifuged immediately at 4° C. and the plasma was stored at −20° C. until conducting the various assays.

DOXIL™ or Zymosan were injected i.v. via the pulmonary catheter, and were washed into the circulation with 10 mL of Ringer solution.

Figure 3A:
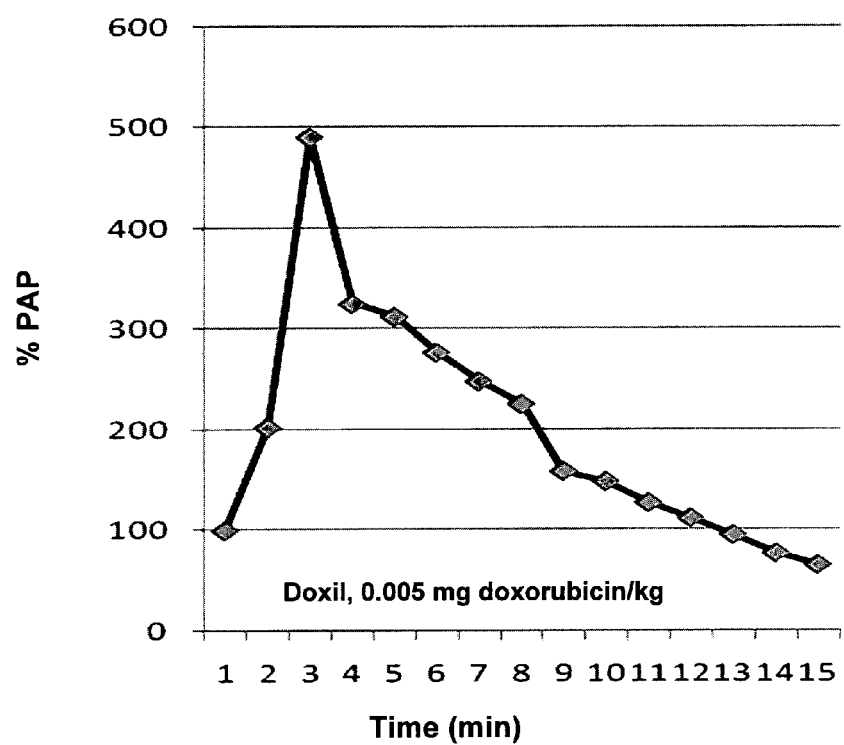
FIGS. 3A-3C. DOXIL™ induces hypersensitivity reactions upon first exposure even to low doses.

FIG. 3A shows that i.v. bolus injection of DOXIL™ (0.005 mg doxorubicin/kg=0.04 mg liposome lipid/kg=0.032 mg liposomal phospholipid/kg) in a pig induced an abrupt, 5-fold (500%) rise of PAP (50 mm Hg) 2-3 minutes after the injection. This rise represents near maximal physiologically tolerable blood pressure in the pulmonary circulation. The PAP values returned to baseline within 12-15 minutes, attesting to the transient nature of the circulatory response. Essentially similar reactions were seen in 6 different experiments performed according to the same procedure (rise of PAP 340+/−50%, n=6 animals from the same cohort), demonstrating remarkable within-cohort reproducibility of the pulmonary hypertensive effect of DOXIL™, administered for the first time at 0.005 mg doxorubicin/kg dose. The inter-cohort (inter-batch)-variation of the maximal reactogenic first dose of DOXIL™ is between 0.005 and 0.015 doxorubicin/kg, while in other animals it may be different. In dogs, for example, (as shown below in Example 7) the maximal pulmonary reactogenic first dose of DOXIL™ may be an order of magnitude higher (0.1 mg doxorubicin/kg).

Figure 3B:
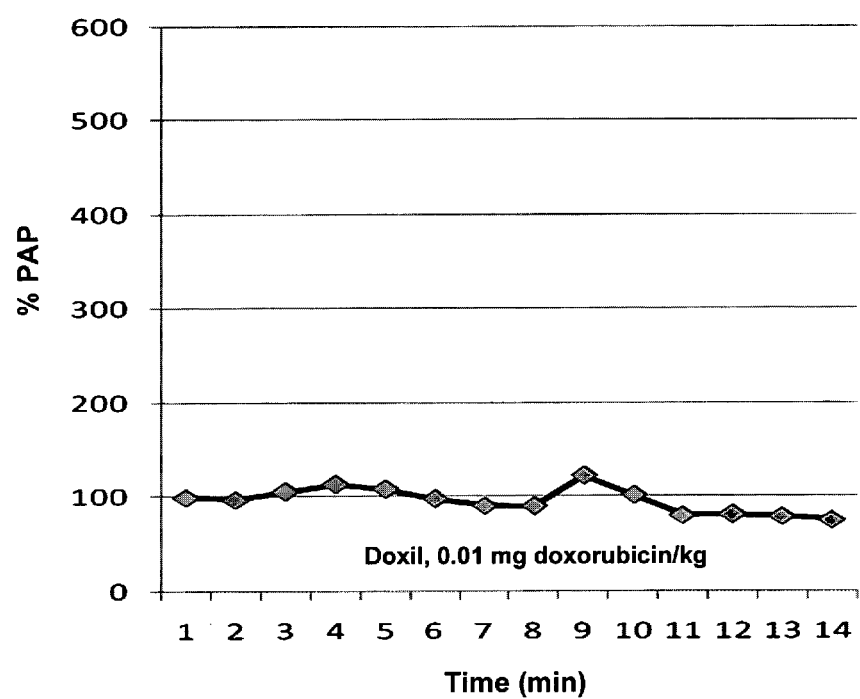
Figure 3C:
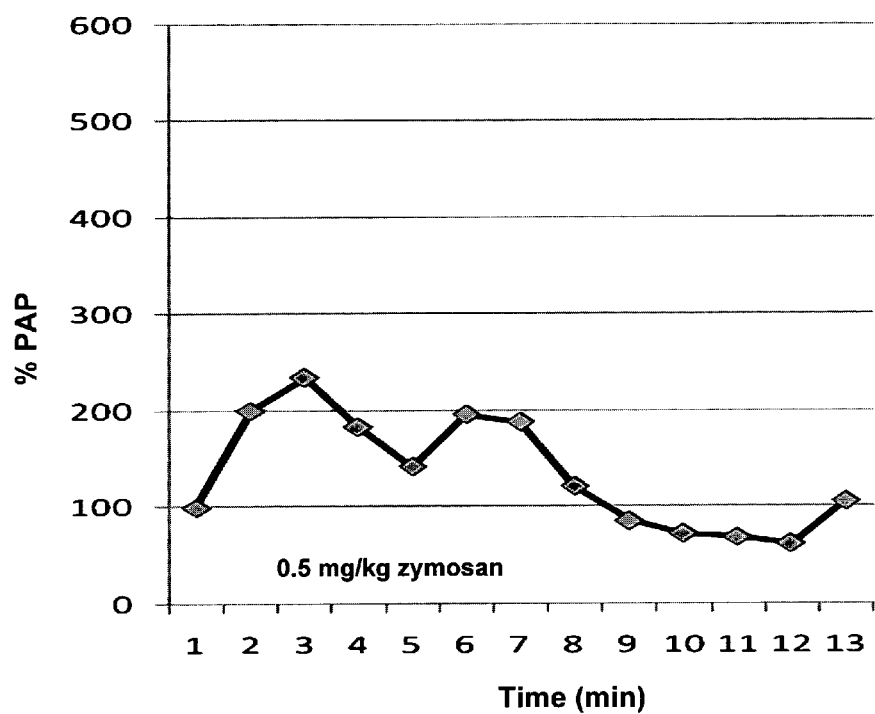

FIG. 3B shows that in sharp contrast to the pulmonary hypertensive effect of maximal reactogenic first dose, 0.01 mg doxorubicin/kg DOXIL™ (i.e. doubled dose) administered 10 minutes after PAP return to baseline following the first reaction, caused either no or minimal (>20%) rise of PAP. Thus, the first injection desensitized the animal in a manner that practically abolished the reaction to the second injection at even higher dose, when administered shortly thereafter. In order to verify that the above tolerance was specific for DOXIL™, an injection of Zymosan (0.5 mg/kg) instead of a second dose of DOXIL™ was tested showing absence of the tolerance, namely a significant (up to 250% of baseline) rise of PAP (FIG. 3C).

Example 3

Prevention of Hypersensitivity Reaction to DOXIL™ by Prior Administration of Placebo Liposomes (Doxebo)

The experiment presented in this example shows that drug-free, DOXIL™-equivalent liposomes called herein placebo DOXIL™, or Doxebo, were similar to DOXIL™ in terms of desensitization of pigs for further DOXIL™ reactions. The preparation of Doxebo was performed as described below, such that its physicochemical properties are essentially comparable to those of DOXIL™. Doxebo was consequently tested for its tolerizing effect in experiments similar to those described in Example 2. The lipid components of DOXIL™ were also used to prepare Doxebo, namely HSPC from Lipoid Inc., Ludwigshafen, Germany (purity ≥97%). 2K-PEG-DSPE either from Lipoid or from Genzyme, Liestal, Switzerland and cholesterol from Sigma. HSPG, used in some control experiments instead of 2K-PEG-DSPE, was from Lipoid Inc. The lipids were mixed in ethanol at 65° C. to a final mole ratio of 52.8:4.5:42.7, respectively. After sterile filtration through a 0.2 micron filter, the lipid solution was added into 10 volumes of 10% sucrose and incubated for 30-60 minutes at 65° C., with stirring. The large multilamellar liposomes formed upon hydration were than extruded sequentially first through 0.4 and than through 0.1 μm pore sized polycarbonate filters at 70° C., using a Lipex "Extrude". Extrusion through 0.4 and 0.1 μm filters were repeated 4 or 10 times, respectively. Finally, the ethanol was removed by few steps of dialyses at 4° C.

Physicochemical comparison of DOXIL™ and Doxebo was performed by measuring size distribution and zeta potential of DOXIL™ and Doxebo. Size was determined by dynamic light scattering, using a Malvern ZetaSizer 4 (5-mW power, He—Ne, k=633 nm, laser source).

Zeta, (ζ) potential was measured at 25° C. using a Zetasizer 3000 HAS, Malvern Instruments Ltd, (Malvern, UK. Liposomes). Specifically, 40 μL of the original dispersion were diluted in 20 mL of filtered (0.2-μm) 10 mM NaCl (pH 6.7). These dispersions were filtered through a 0.2-μm syringe filter (Minisart, Sartorius, Germany).

All liposomes were characterized by determining their electrical surface potential ($\Psi_0$) by measuring 4-heptadecyl-7-hydroxycoumarin (HC) ionization over a broad range of pH values as described by Zuidam and Barenholz 1997 (Zuidam, N.J. and Barenholz, Y. 1997). Specifically, an aliquot of 30 μl, of HC labeled liposomes was diluted in 1.5 mL of Hepes buffer, the pH was adjusted to 7.4 by addition of an appropriate amount of concentrated sodium hydroxide and hydrochloric acid and the samples were sonicated for about 5 seconds in a water bath to ensure pH equilibration between the interior and exterior of the vesicles. To measure the HC ionization state, HC fluorescence excitation spectra were recorded at room temperature (22° C.) using an LS550B luminescence spectrometer (Perkin Elmer, Norwalk, Conn.). Measurements were carried out at two excitation wavelengths: 330 nm, which is pH independent (isosbestic point) and represents the total amount of HC (un-ionized+ionized) in the lipid environment, and 380 nm, which reflects only the ionized HC⁻. The emission wavelength was 450 nm for both excitation wavelengths. Excitation and emission bandwidths of 2.5 nm were used. For each lipid composition, the apparent pKa of HC was calculated from the change in the ratio of excitation wavelengths 380/330 as a function of bulk pH. A shift in the apparent pKa of HC, which correlates to proton binding constant, relative to a reference neutral surface, is indicative of the surface pH and the electrical surface potential in the immediate environment of the HC fluorophore. The values for electrical surface potential ($\Psi$) were calculated using the equation:

$$\Psi_0 = -\frac{\Delta pK_{el}kT}{e\ln 10}$$

The size distribution of DOXIL™ and Doxebo were similar. Table 3 specifies the derived mean sizes, the polydispersity indices (PDI) and $\zeta$ values. The data reveals slightly smaller mean size and narrower size distribution, corresponding to lower polydispersity of DOXIL™ compared to Doxebo. The zeta potential of DOXIL™ was lower then the zeta potential of Doxebo. Nevertheless, a comparison of the mean size of 3 different DOXIL™ and Doxebo preparations showed no statistical difference between the groups (DOXIL™, 108±33 nm, Doxebo, 124±25 nm). The zeta potential values were similar, namely both are slightly negatively charged (−13.3±2.5 and −10.1±2.5 my for DOXIL™ and Doxebo respectively), significantly less negatively charged than liposomes of identical lipid composition in which the 2K PEG-DSPE was replaced by hydrogenated soy phopshatidylglycero (HSPG, Gurbezenko et al. 2005).

Electrical surface potential $\Psi_0$ value for Doxebo was −52 mV (similar to liposomes of identical lipid composition in which the 2K PEG-DSPE was replaced with HSPG (Gubenzeko et al. 2005), $\Psi_0$ value for DOXIL™ could not be determined because of the interference of doxorubicin to the measurement of fluorescence intensity.

TABLE 3

Composition and physicochemical characteristics of DOXIL ™ and Doxebo:

| Liposome | Size (nm) | polydispersity indices (PDI) | ($\zeta$) (mV) |
|---|---|---|---|
| DOXIL ™ | 108 ± 33 | 0.06 | −13.3 ± 2.5 |
| Doxebo | 124 ± 25 | 0.10 | −10.1 ± 2.5 |

Taken together, these physicochemical tests show that DOXIL™ and Doxebo have minor, statistically insignificant differences in their size, size distribution and surface electric properties. These small differences can be attributed to an inevitable difference between bench top and industrial production of DOXIL™. Doxebo are thus referred to as DOXIL™ placebo liposomes.

To test the tolerizing effect of placebo DOXIL™ in pigs, in vivo studies similar to those described in Example 2 were performed, except for the replacement of DOXIL™ first bolus injection with Doxebo.

Figure 4:
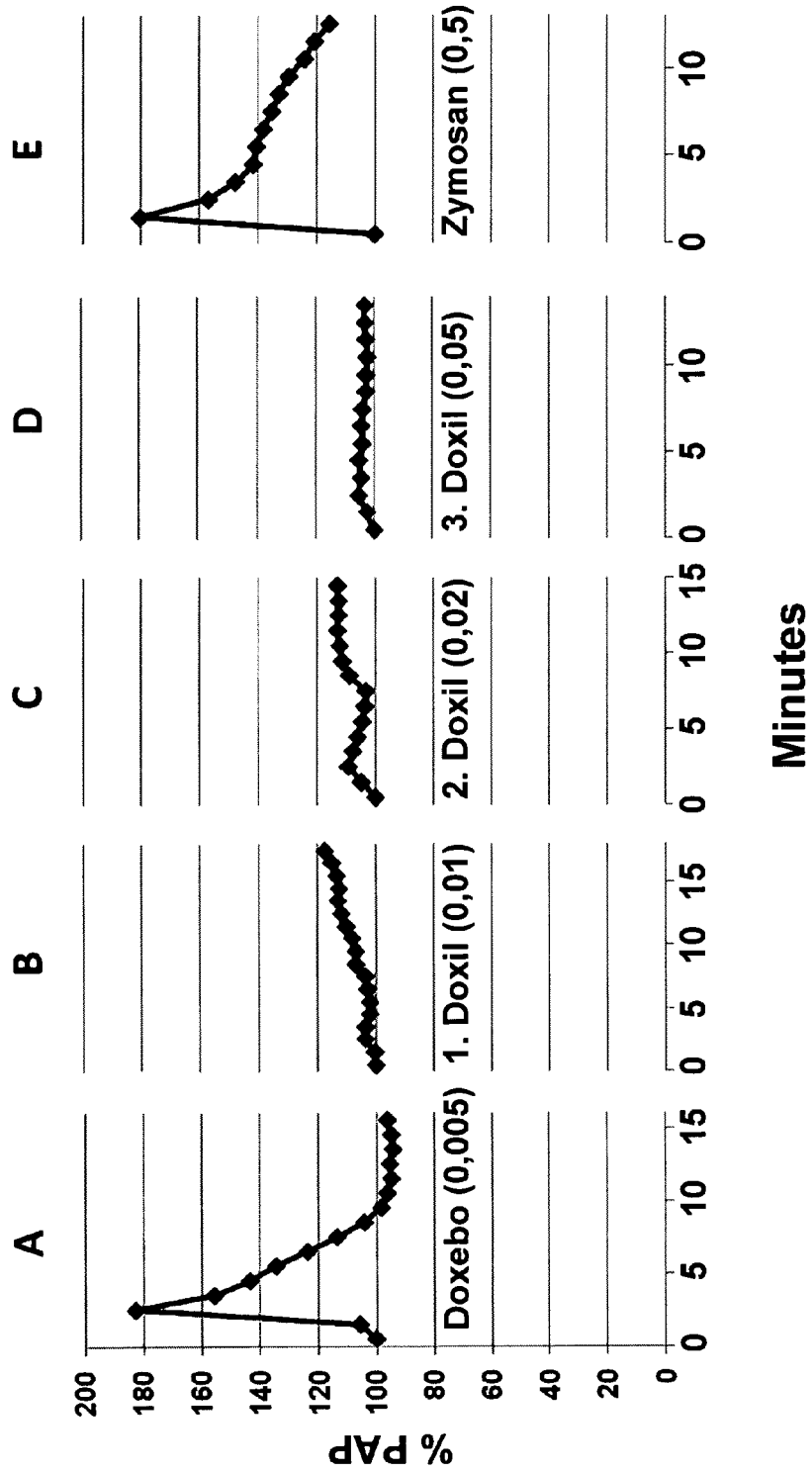
FIG. 4. Prevention of DOXIL™-induced pulmonary hypertension by i.v. bolus administration of Doxebo. Doxebo was administered by i.v. bolus (panel A) followed by three i.v. bolus injections of increasing amounts of DOXIL™ (panels B-D) (doses are in mg doxorubicin/kg pig for DOXIL™, or in case of Doxebo, the doses are in mg lipid/kg or mg phospholipid/kg equivalent to the amount of liposomal lipid found in DOXIL™). The arrows indicate the time of injections. Zymosan injection (panel E) was tested as positive control demonstrating that the animal did not lose cardiovascular responsiveness as a consequence of desensitization.

FIG. 4 shows the results of an experiment wherein a pig was administered by i.v. bolus 0.002 mg doxorubicin/kg DOXIL™'s equivalent Doxebo (0.016 mg liposomal lipid/kg), a dose equal to 40% of DOXIL™'s maximal tolarated first dose. This injection caused 80% rise of PAP, which is about one sixth of the maximal hypersensitivity reaction, suggesting that Doxebo is less reactogenic than DOXIL™. Subsequent bolus injections of DOXIL™ at increasing doses, i.e., 0.01, 0.02 and 0.05 mg doxorubicin/kg caused no abrupt rise of PAP, attesting to tolerance. Finally, injection of 0.5 mg/kg Zymosan did cause a major reaction (rise of mean PAP from 18 to about 46 mmHg), attesting to specific desensitization, similar to that seen in Example 2. Thus, Doxebo, administered as bolus at a phospholipid dose 60% lower than DOXIL™'s maximally reactogenic dose, entirely desensitized the animal for subsequent reactions caused by DOXIL™, injected at doses 2-5-times higher than the maximally reactogenic dose. In sum, these experiments demonstrate that although bolus administration of Doxebo was reactogenic, the reaction caused by Doxebo was smaller in comparison to that caused by DOXIL™, yet the tolerizing effect was the same as caused by DOXIL™, namely, full desensitization for doses up to 5-fold larger than the maximally reactogenic dose of DOXIL™.

Example 4

Prevention or Attenuation of Hypersensitivity Reaction to DOXIL™ in Pigs by Prior Slow Injection of Placebo DOXIL™

Figure 5:
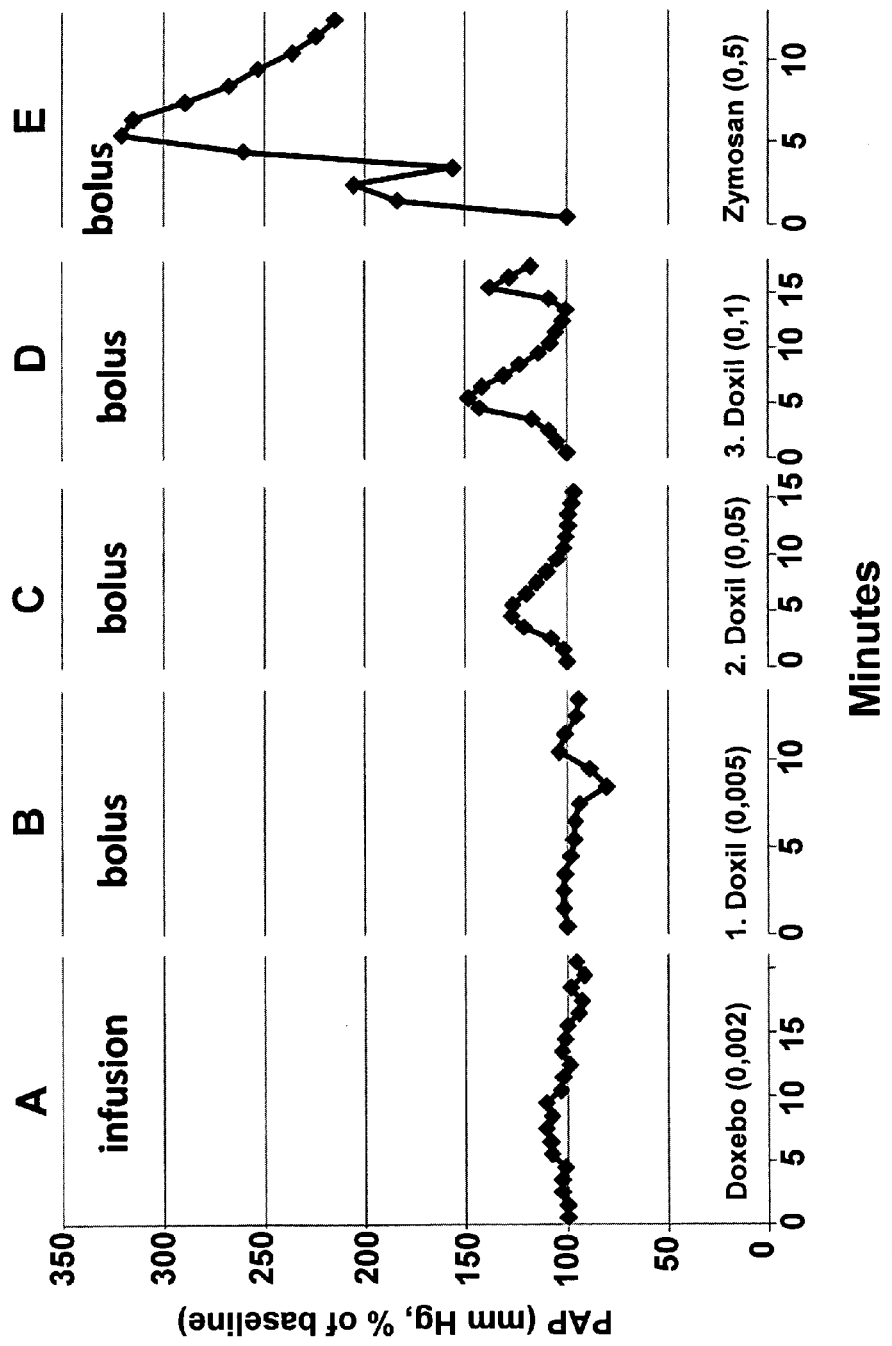
FIG. 5. Prevention of DOXIL™-induced pulmonary hypertension by Doxebo, administered by i.v. infusion. Doxebo was administered to a pig by i.v. infusion at a rate of approximately 5 microgram/min (panel A) followed by three i.v. bolus of increased amounts of DOXIL™ (panels B-D) (doses are in mg doxorubicin/kg pig). Zymosan injection (panel E) was tested as control demonstrating that the animal did not lose cardiovascular responsiveness as a consequence of desensitization to DOXIL™.

Panel A of FIG. 5 shows a similar experiment as described in Example 5, except that Doxebo was administered slowly, via i.v. infusion over 10 minutes. Similarly, Doxebo caused tolerance to subsequent DOXIL™ reactions inasmuch as it entirely prevented the reaction to 0.005 mg doxorubicin/kg DOXIL™ (FIG. 5, panel B), and significantly reduced the reactions to DOXIL™ i.v. boluses of 10 (FIG. 5, panel C) and even 20-fold (FIG. 5, panel D) higher amounts of liposomes. The final 0.5 mg/kg Zymosan bolus, on the other hand, caused the same strong response as seen in Examples 2 and 3 (FIG. 5, panel E), showing that the animal was responsive to the complement activating trigger, the lack or reduced pulmonary responses were not due to inherent allergy of the animal or as a result of a technical error.

Example 5

Reproducibility of Desensitization

In order to establish the reproducibility of the desensitizing effect of Doxebo, the DOXIL™ reactions were quantified by scoring the cardiac and hemodynamic symptoms on an arbitrary scale in 1-5 range. The concept and calculation of cardiac abnormality score values (CAS) were described earlier (Szebeni et al., 2006) and are shown in Table 4. These scores take into consideration all cardiopulmonary and hemodynamic changes and differentiate CAS according to increased severity from mild to lethal.

TABLE 4

Quantification of liposome-induced cardiac abnormalities in pigs.

| ECG Abnormalities | Hemodynamic and Cardiorespiratory Alterations | Qualitative description | CAS* |
|---|---|---|---|
| Arrhythmia episodes, transient tachycardia | Minimal or no changes in PA, SAP, CO, PAP and pCO$_2$. | Minimal | 1 |
| Longer lasting arrhythmia with tachycardia | Moderate rise of SAP and reduction of PA, minimal or no changes in CO, PAP and pCO$_2$ | Mild | 2 |
| Major arrhythmias with tachycardia and/or bradycardia | Initial rise followed by moderate declines in SAP, PA, CO and pCO$_2$, moderate rise of PAP | Moderate | 3 |
| Major arrhythmias with tachycardia and/or bradycardia, ST depression/T wave changes | Dramatic and extended declines in SAP, PA, CO and pCO$_2$, major rise of PAP | Severe | 4 |
| Major arrhythmias with tachycardia and/or bradycardia, ST | Dramatic, extended and irreversible declines in SAP, PA, CO and pCO$_2$, maximal | Lethal | 5 |

TABLE 4-continued

Quantification of liposome-induced cardiac abnormalities in pigs.

| ECG Abnormalities | Hemodynamic and Cardiorespiratory Alterations | Qualitative description | CAS* |
|---|---|---|---|
| depression/T wave changes, cardiac arrest with or without ventricular fibrillation | rise of PAP. Fatal without CPR** | | |

(from Szebeni et al., 2006)
Abbreviation used for this table: CPR, cardiopulmonary resuscitation; PA, arterial pressure amplitude.
*CAS, cardiac abnormality score, an arbitrary rank based on the severity of ECG (column 1) and associated hemodynamic and cardiorespiratory abnormalities (column 2).
**Adminsitration of i.v. epinephrine (0.01-0.1 mg/kg) with or without chest compression and/or electroconversion.

Table 5 shows (using the scoring described in Table 4) that all five control pigs injected with 0.005-0.01 mg doxorubicin/kg DOXIL™ as first i.v. bolus, showed cardiac abnormality score (CAS) of 3-4, namely moderate to severe reactions. Out of 13 pigs evaluated using Doxebo administered at 0.002-0.006 mg doxorubicin/kg equivalent lipid doses (0.016-0.048 mg lipid/kg), 10 pigs showed no pulmonary reaction to a second i.v. bolus of 0.005-0.01 mg doxorubicin/kg DOXIL™ (CAS=0). The remaining three experienced a significantly weaker reaction (CAS=1) than seen in the non-desensitized control. Of the 13 pretreated animals, Doxebo was administered by slow i.v. infusion or i.v.bolus to 4 and 9 cases respectively. All 9 pigs who obtained Doxebo by i.v bolus developed a reaction corresponding to CAS grade of 1-2, while only one out of 4 pigs treated with Doxebo by slow i.v. injection developed a reaction corresponding to CAS=2. This data suggests that minor amounts of Doxebo can either completely eliminate or reduce the risk of DOXIL™-induced CARPA. Although Doxebo can by itself be slightly reactogenic, this minor reactogenicity can be further reduced by slow i.v. infusion of Doxebo rather than by i.v.bolus.

TABLE 5

Reproducibility of Doxebo's tolerance induction for DOXIL ™ reactions.

| Pre-treatment | Mode of administration | Reaction | | | |
|---|---|---|---|---|---|
| | | Doxebo (0.016-0.048 mg lipid/kg) | | DOXIL ™ (0.005-0.01 mg doxorubicin/kg, 0.04-0.08 mg lipid/kg) | |
| | | No./all | CAS | No./all | CAS |
| None | | | | 5/5 | 3-4 |
| Doxebo | Bolus | 1/9 | 0 | | |
| Doxebo | Bolus | 9/9 | 1-2 | 10/13 | 0 |
| Doxebo | Infusion | 3/4 | 0 | 3/13 | 1 |
| Doxebo | infusion | 1/4 | 2 | | |

Example 6

Endurance of Tolerance

Figure 6:
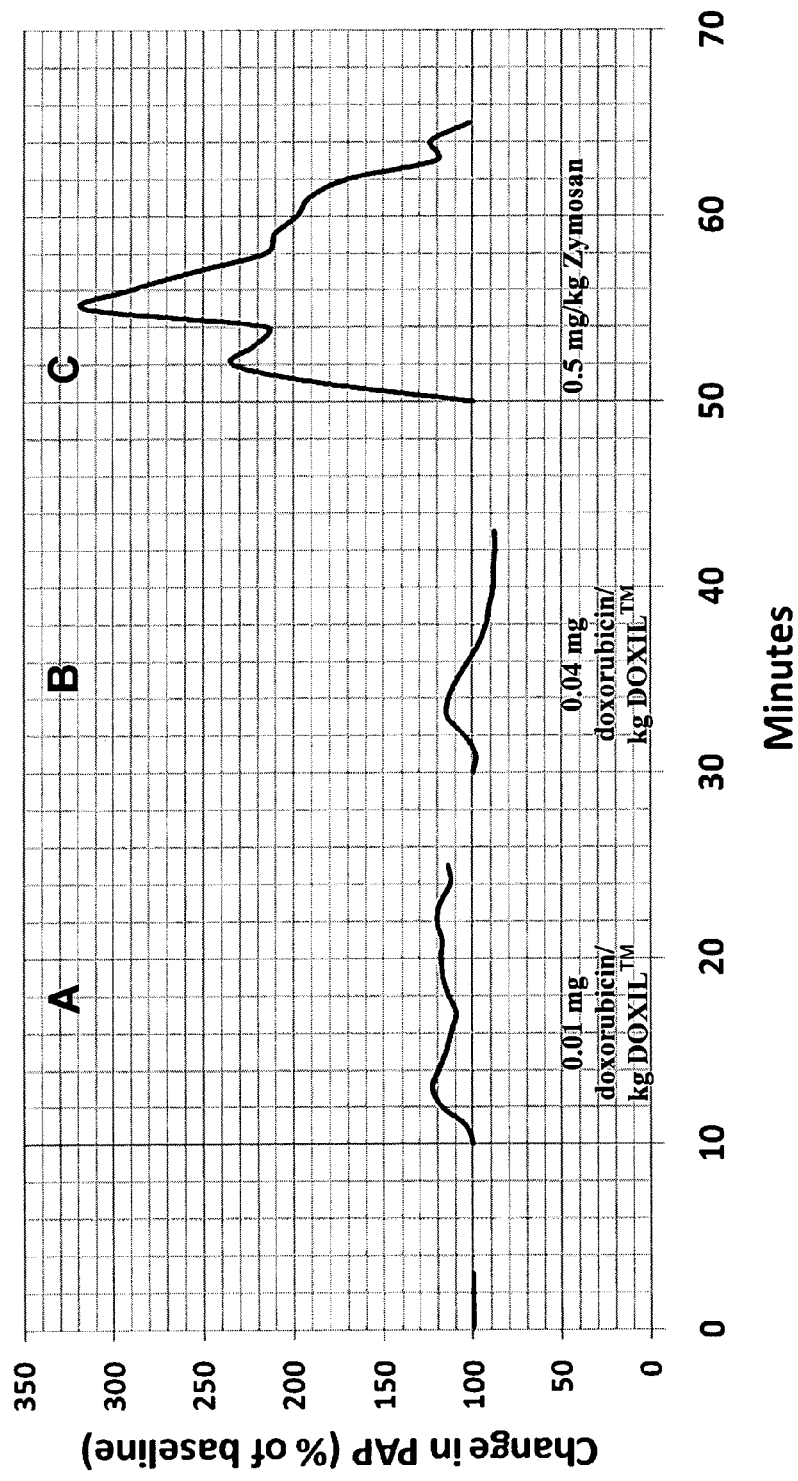
FIG. 6. Prevention of DOXIL™-induced pulmonary hypertension by Doxebo, administered 24 hours before treatment with DOXIL™. Doxebo was injected to a pig by i.v. bolus 24 hours before the i.v. bolus administration of DOXIL™ (panels A and B) (doses are in mg doxorubicin/kg pig). Zymosan injection was tested as positive control (panel C).

In an effort to establish the time window of tolerance induction, Doxebo was injected to a pig, 24 hours before the first DOXIL™ administration. This pretreatment prevented the reactogenicity toward 0.01 and 0.04 mg doxorubicin/kg DOXIL™ (FIG. 6, panels A and B). Based on this observation it is possible to tolerize pigs against DOXIL™ reactions 24 hours before treatment. 0.5 mg/kg Zymosan administered afterwards by i.v. bolus, caused the same strong response as seen in Examples 2, 3 and 4 (FIG. 6, panel C), showing that the animal was responsive to complement activating trigger, and the lack or reduced pulmonary response was not due to inherent allergy of the animal or as a result of a technical error.

Example 7

Induction of Tachyphylactic Liposome Reactions in Dogs with DOXIL™

In an effort to explore the species dependence of tolerance induction against DOXIL™ reactions, dogs were injected with DOXIL™ in a manner similar to the procedure described above for pigs. As shown in Table 6, the dose that is reactogenic in pigs (0.01 mg doxorubicin/kg) caused only minor (16%) rise of PAP (dog #1), suggesting that the pulmonary response of dogs is less sensitive to DOXIL™ than that of pigs. However, a 10-fold higher dose (0.1 mg doxorubicin/kg) caused pulmonary hypertension similar to that observed in pigs (73% rise of PAP over baseline), and the reaction was tachyphylactic inasmuch as the 2nd similar injection caused only 32% rise of PAP (dog 2). Zymosan, on the other hand, retained its efficacy in terms of rise in PAP by 77%. Considering that self-tolerance induction (whose manifestation is tachyphylaxis), is a precondition for the efficacy of Doxebo in pigs (as shown in example 2), these data provide indirect evidence that tolerization for DOXIL™ reactions with Doxebo is also possible in dogs.

TABLE 6

Pulmonary pressure responses in dogs to repeated bolus administration of DOXIL ™.

| Dog | | DOXIL ™ | | | | | | | | Zymosan | | | |
|---|---|---|---|---|---|---|---|---|---|---|---|---|---|
| | | 1st injection | | | | 2nd injection | | | | 1st injection | | | |
| # | Weight (kg) | Dose (mg/kg*) | Before (mm Hg) | Maximal (mm Hg) | % rise | Dose (mg/kg* | Before (mm Hg) | Maximal (mm Hg) | % rise | Dose (mg/kg*) | Before (mm Hg) | Maximal (mm Hg) | % rise |
| 1 | 22 | 0.01 | 21.1 | 24.5 | 116 | 0.01 | 26.6 | 28.6 | 107 | 2.5 | 24.9 | 30.7 | 139 |
| 2 | 25 | 0.1 | 18.6 | 32.1 | 173 | 0.1 | 18.4 | 24.3 | 132 | 5.0 | 18.0 | 31.8 | 177 |

*mg doxorubicin/kg

Example 8

Tolerization of Dogs Against DOXIL™ Reaction with Empty Liposomes

To confirm the suggestion made on the basis of tachyphylactic cardiopulmonary response to DOXIL™, namely that placebo liposomes can tolerize dogs against DOXIL™ reactions, we injected one dog with DOXIL™ and a second dog with empty pegylated liposomes, as tolerizing agents, followed in both cases by 2 sequential injections of DOXIL™ in a manner similar to the procedure described above for pigs. In the experiment presented in Table 7 the empty, PEGylated liposomes (containing egg yolk phosphatidylcholine (EPC) instead of hydrogenated soy lecithin (HSPC), the standard phospholipid component of DOXIL™), caused 60% drop of SAP within 3 minutes, a sign of reactogenicity, just as seen in pigs The 2nd injection of the same amount of DOXIL™ caused <10% drop of SAP, providing evidence for tolerization by the first injection. Similar effect was observed in dog #2, in which empty EPC/Chol/PEG-PE liposomes were injected. In both animals, the major reaction caused by final injection of zymosan attested to the specificity of tolerization in terms of not tolerizing against non-liposomal reactions, such as caused by the yeast cell membrane extract, zymosan. The experiment proves that DOXIL™, as well as pegylated small unilamellar liposomes which largely, but not exactly mimic the size and PEG content of DOXIL™ but not its lipid composition, can induce tolerance against DOXIL™ in dogs.

TABLE 7

Tolerization of dogs against DOXIL ™ reactions by prior administration of DOXIL ™ or equivalent empty PEGylated liposomes.

| Dog | 1st injection | | | 2nd injection | | | Last injection | | |
|---|---|---|---|---|---|---|---|---|---|
| | trigger | dose | % decrease of SAP | trigger | dose | % decrease of SAP | trigger | dose | % decrease of SAP |
| 1 | DOXIL ™ | 0.1 mg/kg | 60 | DOXIL ™ | 0.1 mg/kg | <10% | zymosan | 0.5 mg/kg | >50% |
| 2 | EPC/Chol/PEG-PE* | | 5 | | | | | | |

*EPC/Chol/PEG-PE, Small unilamellar (100 nm diameter) liposomes containing 10% mole PEG-PE. Mg/kg refer to mg doxorubicin/kg or equivalent amount of lipid.

Example 9

Figure 7:
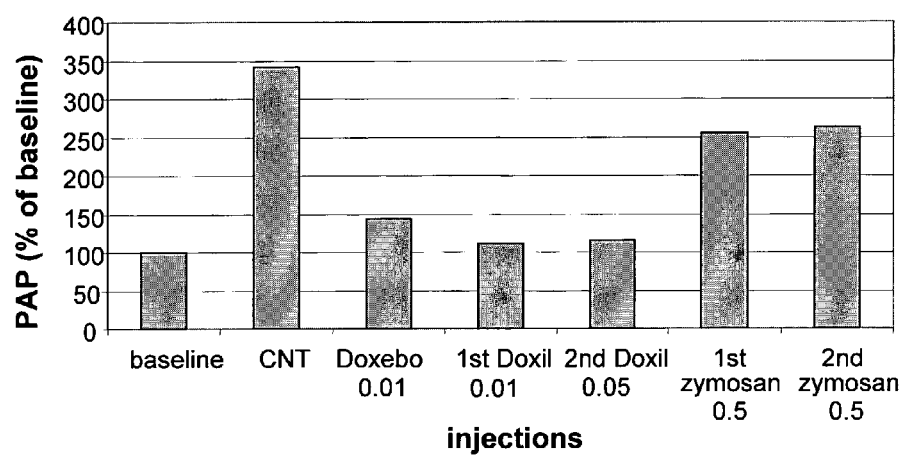
FIG. 7. Pulmonary hypertensive effects of serial i.v. bolus administrations of a non-liposomal complement activator (Multiwall carbon nanotubes, MWCNT) followed by Doxebo, DOXIL™ and Zymosan. (doses are in mg doxorubicin/kg pig or, in case of Doxebo, 0.08 mg lipid/kg or 0.064 mg/kg phospholipid/kg (i.e., liposomal lipid equivalent to that found in 0.01 mg/kg DOXIL™).

Carbon Nanotubes do not Tolerize Dogs Against Hypersensitivity Reactions Caused by Liposomal Activators Nonliposomal complement activators do not cross tolerize dogs against hypersensitivity reactions caused by liposomal complement activators. FIG. 7, demonstrates a major pulmonary hypertensive response caused by i.v. bolus injection of 1 mg/kg non-liposomal complement activator, multiwall carbon nanotubes (MWCNT), to a dog. The administration of MWCNT prior to the administration of Doxebo did not tolerize the dog against the minor hypersensitivity reactions caused by Doxebo. This is shown by the relatively small, but significant pulmonary response (40% rise of PAP) to the i.v. bolus of Doxebo. The subsequent lack of reaction towards DOXIL™ is consistent with Doxebo's tolerizing effect. This experiment therefore provides proof that MWCNT do not cross tolerize dogs against hypersensitivity reactions caused by liposomal complement activators. Thus, small unilamellar pegylated liposomes, such as Doxebo, are specific in toleriz ing against hypersensitivity reactions caused upon administration of DOXIL™.

Example 10

In Vitro Evidence for Reduced Complement Activation by Doxebo

Figure 8A:
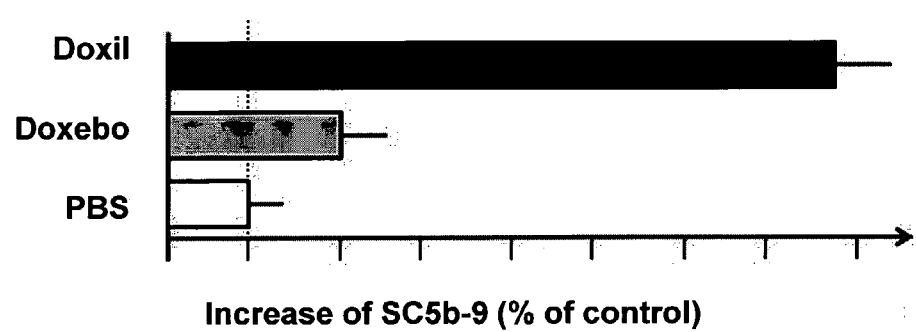
FIG. 8A shows the large effects of DOXIL™ versus little or no effect of Doxebo in one human serum (Mean+/−SD, n=3).
Figure 8B:
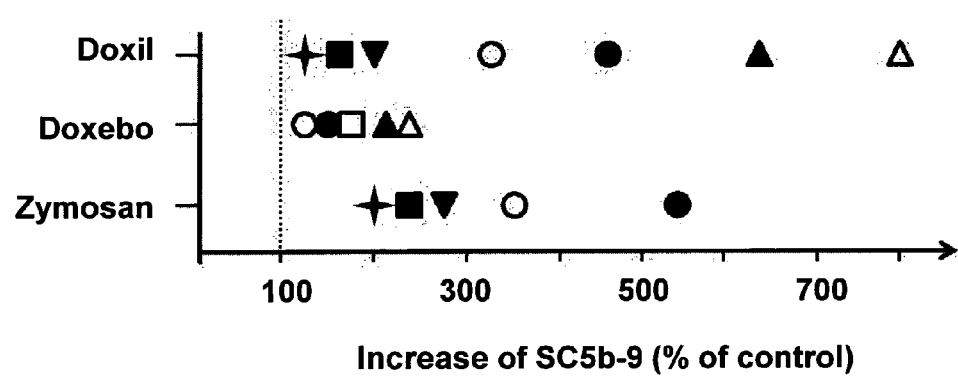
FIG. 8B shows the individual variation of the responses, in up to 7 different human sera. Different symbols denote different donors. All values were related to PBS control taken as 100% (dotted lines).

Considering the postulated relationship between complement activation and hypersensitivity reaction in pigs, the examples presented above suggest that Doxebo is less potent complement activator than DOXIL™. To better evaluate this proposition, complement activating capabilities of DOXIL™ were compared vs. Doxebo in vitro, using normal human serum as a complement source. The source of DOXIL™ and preparation of Doxebo were performed as described in Examples 2 & 3. DOXIL™ or Doxebo (10 μL from the 13 mg phospholipid/mL liposome stocks) were mixed with undiluted human serum (40 μL) in Eppendorf tubes, following their incubation for 30 minutes at 37° C. in an ultrasonic bath (shaking rate of 80 rpm). For negative control phosphate-buffered saline (PBS) was used instead of liposomes. The reaction was stopped by adding 20 volumes of 10 mM EDTA, 25 mg/mL bovine serum albumin, 0.05% Tween 20 and 0.01% thimerosal (pH 7.4), and complement activation was estimated by measuring the formation of S protein-bound C5b-9 (SC5b-9), a well-known marker of full activation of the complement cascade to the terminal complex (Szebeni et al., 2003). SC5b-9 was determined by an enzyme-linked immunosorbent assay (ELISA, Quidel Co., San Diego, Calif.). FIG. 8A shows one human serum wherein DOXIL™ caused a significant (7-fold) increase of SC5b-9 over PBS control. Doxebo also caused significant complement activation, but its effect was considerably less than that of DOXIL™. FIG. 8B shows the same phenomenon in 5-7 different sera, illustrating the individual variation, yet consistency of DOXIL™'s larger complement activating effect compared to Doxebo. The example demonstrates that Doxebo is a less potent activator of the human complement than DOXIL™. This might provide an explanation for its weaker reactogenicity in pigs. Moreover, a decrease in the human complement activation is potentially of high importance for possible human application as a desensitizer agent.

While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES

Avnir Y, Ulmansky R, Wasserman V, Even-Chen S, Broyer M, Barenholz Y, Naparstek Y. (2008) Amphipathic weak acid glucocorticoid prodrugs remote-loaded into sterically stabilized nanoliposomes evaluated in arthritic rats and in a Beagle dog: a novel approach to treating autoimmune arthritis. Arthritis Rheum 58(1):119-29.

Christine Allen, Dusica Maysinger, Adi Eisenberg (1999) Nano-engineering block copolymer aggregates for drug delivery: Colloids and Surfaces B: Biointerfaces, 16(1-4) 3-27.

Bangham A D, Standish M M, Watkins J C. (1965) Diffusion of univalent ions across the lamellae of swollen phospholipids. J Mol Biol. 13(1):238-52.

Barenholz, Y. & Cevc, G. (2000) Structure and properties of membranes in Physical Chemistry of Biological Surfaces. Marcel Dekker, New York.

Brouwers, A. H., De Jong, D. J., Dams, E. T., Oyen, W. J., Boerman, O. C., Layerman, P., Naber, T. H., Storm, G., and Corstens, F. H. (2000): Tc-99m-PEG-Liposomes for the evaluation of colitis in Crohn's disease. J Drug Target 8, 225-33.

Cabriales, S., Bresnahan, J., Testa, D., Espina, B. M., Scadden, D. T., Ross, M., and Gill, P. S. (1998): Extravasation of liposomal daunorubicin in patients with AIDS-associated Kaposi's sarcoma: a report of four cases. Oncol Nurs Forum 25, 67-70.

Chanan-Khan, A., J. Szebeni, J., Leibes, L., Rafique, M., Savay, S., Alving, C. R., and Muggia, F. M. (2001): Complement activation by pegylated liposomal doxorubicin (DOXIL™) in cancer patients: association with hypersensitivity reactions. J. Contr. Drug Rel. abstract in press.

Cheifetz A, Mayer L. (2005) Monoclonal antibodies, immunogenicity, and associated infusion reactions. Mt Sinai J Med. 72(4):250-6.

Clerc S, Barenholz Y. (1995) Loading of amphipathic weak acids into liposomes in response to transmembrane calcium acetate gradients. Biochim Biophys Acta. 1240(2): 257-65.

Coombs, R. R. A., and Gell, P. G. H. (1968): Classification of allergic reactions responsible for drug hypersensitivity reactions, pp. 575-596. In R. R. A. Coombs, and P. G. H. Gell (Eds): Clinical Aspects of Immunology, 2$^{nd}$ Ed., Davis, Philadelphia, Pa.

Deamer D, Bangham A D. (1976) Large volume liposomes by an ether vaporization method. Biochim Biophys Acta. 443 (3):629-34.

Descotes, J., and Choquet-Kastylevsky, G. (2001): Gell and Coombs's classification: Toxicology 158, 43-49.

Guaglianone, P., Chan, K., DelaFlor-Weiss, E., Hanisch, R., Jeffers, S., Sharma, D., and Muggia, F. (1994): Phase I and pharmacologic study of liposomal daunorubicin (DaunoXome). Invest New Drugs 12, 103-110.

Haran G, Cohen R, Bar L K, Barenholz Y. (1993) Transmembrane ammonium sulfate gradients in liposomes produce efficient and stable entrapment of amphipathic weak bases. Biochim Biophys Acta. 1151(2):201-15.

Christopher Kirby and Gregory Gregoriadis (1984) Dehydration-Rehydration Vesicles: A Simple Method for High Yield Drug Entrapment in Liposomes. Nat. Biotechnol. 2, 979-984.

Janoff A. S. (1999) Liposomes-Rational Design-Janoff, A. S. (Ed.), Marcel Dekker, New York.

Kirschfink, M. (1997): Controlling the complement system in inflammation. Immunopharmacology 38, 51-62.

Lenz H. J. (2007): Management and preparedness for infusion and hypersensitivity reactions. Oncologist 12(5):601-9.

Lavasanifar A, Samuel J, Kwon G S. (2000) Micelles of poly(ethylene oxide)-block-poly(N-alkyl stearate L-aspartamide): synthetic analogues of lipoproteins for drug delivery: J Biomed Mater Res. 52(4):831-5.

Moghimi S M, Hamad I, Andresen T L, Jorgensen K, Szebeni J. (2006) Methylation of the phosphate oxygen moiety of phospholipid-methoxy(polyethylene glycol) conjugate prevents PEGylated liposome-mediated complement activation and anaphylatoxin production. FASEB J. 20(14): 2591-3

Perkins W R, Ahmad I, Li X, Hirsh D J, Masters G R, Fecko C J, Lee J, Ali S, Nguyen J, Schupsky J, Herbert C, Janoff A S, Mayhew E. (2000) Novel therapeutic nano-particles (lipocores): trapping poorly water soluble compounds. Int. J. Pharm. 200(1):27-39.

Shew R L, Deamer D W. (1985) A novel method for encapsulation of macromolecules in liposomes. Biochim Biophys Acta. 816(1):1-8.

Soppimath K S, Aminabhavi T M, Kulkarni A R, Rudzinski W E. (2001) Biodegradable polymeric nanoparticles as drug delivery devices: J Control Release. 70(1-2):1-20.

Szebeni, J. (2001): Complement activation-related pseudoallergy caused by liposomes, micellar carriers of intravenous drugs and radiocontrast agents. Crit. Rev. Ther. Drug Carr. Syst. 18, 567-606.

Szebeni, J. (2004): Complement activation-related pseudoallergy: Mechanism of anaphylactoid reactions to drug carriers and radiocontrast agents, pp. 399-440. In J. Szebeni (Ed.): The Complement System: Novel Roles in Health and Disease, Kluwer, Boston.

Szebeni, J. (2005): Complement activation-related pseudoallergy: a new class of drug-induced acute immune toxicity. Toxicology 216, 106-121.

Szebeni, J., Alving, C. R., Savay, S., Barenholz, Y., Priev, A., Damino, D., and Talmon, Y. (2001): Formation of complement-activating particles in aqueous solutions of Taxol: Possible role in hypersensitivity reactions. Intern. Immunopharm. 1, 721-735.

Szebeni, J., and Alving, C. R. (1999): Complement-mediated acute effects of liposome-encapsulated hemoglobin. Artif Cells Blood Substit Immobil Biotechnol 27, 23-41.

Szebeni, J., Baranyi, B., Savay, S., Bodo, M., Morse, D. S., Basta, M., Stahl, G. L., Bunger, R., and Alving, C. R. (2000a): Liposome-induced pulmonary hypertension: Properties and mechanism of a complement-mediated pseudoallergic reaction. Am. J. Physiol. 279, H1319-H1328.

Szebeni, J., Baranyi, B., Savay, S., Lutz, L. U., Jelezarova, E., Bunger, R., and Alving, C. R. (2000b): The role of complement activation in hypersensitivity to pegylated liposomal doxorubicin (DOXIL™). J Liposome Res 10, 347-361.

Szebeni, J., Baranyi, L., Bunger, R., Bedocs, P., Toth, M., Rosivall, L., Barenholz, Y., and Alving, C. R. (2007): Animal models of complement-mediated hypersensitivity reactions to liposomes and other lipid-based nanoparticles. J. Liposome Res.

Szebeni, J., Baranyi, L., Sávay, S., Bodó, M., Milosevits, J., Alving, C. R., and Bünger, R. (2006): Complement activation-related cardiac anaphylaxis in pigs: role of C5a anaphylatoxin and adenosine in liposome-induced abnormalities in ECG and heart Function. Am. J. Physiol. 290, H1050-8.

Szebeni, J., Baranyi, L., Savay, S., Milosevits, J., Bodo, M., Bunger, R., and Alving, C. R. (2003): The Interaction of Liposomes with the Complement System: In Vitro and In Vivo Assays. Methods Enzymol. 373, 136-54.

Szebeni, J., Baranyi, L., Savay, S., Milosevits, J., Bunger, R., Layerman, P., Metselaar, J. M., Storm, G., Chanan-Khan, A., Liebes, L., Muggia, F. M., Cohen, R., Barenholz, Y., and Alving, C. R. (2002): Role of complement activation in hypersensitivity reactions to DOXIL™ and HYNIC-PEG liposomes: experimental and clinical studies. J. Liposome Res. In Press.

Szebeni, J., Fontana, J. L., Wassef, N. M., Mongan, P. D., Morse, D. S., Dobbins, D. E., Stahl, G. L., Bünger, R., and Alving, C. R. (1999): Hemodynamic changes induced by liposomes and liposome-encapsulated hemoglobin in pigs: a model for pseudo-allergic cardiopulmonary reactions to liposomes. Role of complement and inhibition by soluble CR1 and anti-05a antibody. Circulation 99, 2302-2309.

Szoka F. C. Jr, Papahadjopoulos D. (1978) Procedure for preparation of liposomes with large internal aqueous space and high capture by reverse-phase evaporation. Proc Natl Acad Sci USA. 75(9):4194-8.

Szoka, F. C. Jr., and Papahadjopoulos D. (1980): Comparative Properties and Methods of Preparation of Lipid Vesicles (Liposomes). Ann. Rev. Biophys. Bioeng. 9, 467-508.

Tirosh, O., Barenholz, Y., Katzhendler, J. & Priev, A. (1998) Hydration of polyethylene glycol-grafted liposomes. Biophys. J. 74, 1371-1379.

Uster P. S. et al. (1996) Insertion of poly(ethylene glycol) derivatized phospholipid into pre-formed liposomes results in prolonged in vivo circulation time FEBS Letters 386, 243-246.

Veronese F. M. and Morpurgo M. (1999) Bioconjugation in pharmaceutical chemistry. Farmaco 54(8): 497-516.

Zuidam N. J. and Barenholz Y. (1997) Electrostatic parameters of cationic liposomes commonly used for gene delivery as determined by 4-heptadecyl-7-hydroxycoumarin. Biochim Biophys Acta. 1329(2):211-22.

The invention claimed is:

1. A method for pretreating an individual at risk of having hypersensitivity reactions associated with administration of a reactogenic pharmaceutical composition comprising a drug or a diagnostic agent formulated within an encapsulated particulate vehicle, the method comprising a desensitizing pretreatment, the desensitizing pretreatment comprising administering to the individual a particulate drug-free vehicle prior to the administration of the reactogenic pharmaceutical composition, wherein the drug-free vehicle is the same vehicle as the vehicle of the reactogenic pharmaceutical composition administered to the individual after the desensitizing pretreatment and wherein the hypersensitivity reactions are accompanied by clinical symptoms selected from the group consisting of anaphylaxis, anaphylactoid reactions, pseudoallergy, infusion reactions, and idiosyncratic reactions, or wherein the hypersensitivity reactions comprise complement system activation-related pseudoallergy.

2. The method according to claim 1, wherein said particulate vehicle is selected from the group consisting of liposomes and micelles; or wherein said particulate vehicle is selected from the group consisting of nanocapsules, nanospheres, block copolymer micelles, polymer lipid hybrid systems, lipid stabilized emulsions and derivatized single chain polymers; or wherein said particulate vehicle is selected from carbon or other nanotubes.

3. The method according to claim 2, wherein said liposomes further comprise stabilizing polymers.

4. The method according to claim 2, wherein said polymers are polyethylene glycol having a molecular weight in the 350-100,000 dalton range.

5. The method according to claim 2, wherein said micelles are selected from the group consisting of lipid micelles, lipoprotein micelles and polymeric micelles.

6. The method according to claim 1, wherein the drug is selected from doxorubicin, daunorubicin, amphotericin B, verteporfin, oxaliplatin, vincristine, topotecan, vinorelbine, paclitaxel, mitoxantrone, c-raf antisense and CTP-11.

7. The method according to claim 1, wherein the particulate vehicle is administered intravenously.

8. The method according to claim 1, wherein said particulate vehicle is administered not more than 7 days, 24 hours, or one hour prior to the administration of said pharmaceutical composition.

9. The method according to claim 1, wherein said particulate vehicle is administered at least once prior to the administration of said pharmaceutical composition.

10. The method according to claim 1, wherein said particulate drug free vehicle does not contain pH gradient liposomes.

* * * * *